United States Patent
Arora et al.

(10) Patent No.: US 9,399,666 B2
(45) Date of Patent: Jul. 26, 2016

(54) INHIBITING INTERACTION BETWEEN THE HIF-1ALPHA AND P300/CBP WITH HYDROGEN BOND SURROGATE-BASED HELICES

(75) Inventors: Paramjit S. Arora, Huntington, NY (US); Bogdan Olenyuk, Sierra Madre, CA (US); Ross N. Chapman, Tuckahoe, NY (US); Laura Henchey, New York, NY (US); Katherine M. Block, Chesterfield, MO (US)

(73) Assignees: New York University, New York, NY (US); The Arizona Board of Regents on Behalf of the University of Arizona, Tuscon, AZ (US)

( * ) Notice: Subject to any disclaimer, the term of this patent is extended or adjusted under 35 U.S.C. 154(b) by 0 days.

(21) Appl. No.: 13/119,108

(22) PCT Filed: Sep. 18, 2009

(86) PCT No.: PCT/US2009/057592
§ 371 (c)(1),
(2), (4) Date: Jun. 20, 2011

(87) PCT Pub. No.: WO2010/033879
PCT Pub. Date: Mar. 25, 2010

(65) Prior Publication Data
US 2011/0245175 A1    Oct. 6, 2011

Related U.S. Application Data

(60) Provisional application No. 61/098,193, filed on Sep. 18, 2008.

(51) Int. Cl.
*A61K 38/00*    (2006.01)
*C07K 14/47*    (2006.01)
*C07K 7/04*    (2006.01)

(52) U.S. Cl.
CPC .............. *C07K 14/4702* (2013.01); *A61K 38/00* (2013.01); *C07K 7/04* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 6,986,881 B1 | 1/2006 | Livingston et al. | |
| 2006/0014675 A1 | 1/2006 | Arora et al. | |

FOREIGN PATENT DOCUMENTS

| | | |
|---|---|---|
| JP | 2008096423 A | 4/2008 |
| WO | 03/100438 A1 | 12/2003 |
| WO | 2005/118620 A2 | 12/2005 |
| WO | 2010/033879 A2 | 3/2010 |
| WO | WO 2010/034028 A1 | 3/2010 |

OTHER PUBLICATIONS

Chapman R. N. et al; "Optimized synthesis of hydrogen bond surrogate helices: Suprising effects of microwave heating on the activity of grubbs catalysts." Organic letters, (2006) 8(25) p. 5825-5828.*
Chapman R. N. et al, supporting information from "Optimized synthesis of hydrogen bond surrogate helices: Surprising effects of microwave heating on the activity of grubbs catalysts." Organic letters (2006) 8(25) p. 5825-5828.*
Freedman, Steven J. et al; "Structural basis for recruitment of CBP/P300 by hypoxia inducible factor-1alpha." PNAS (2002) 99(8) p. 5367-5372.*
Chapman, Ross N. and Arora, Paramjit S.; "Optimized synthesis of hydrogen bond surrogate helices: Surprising effects of microwave heating on the activity of grubbs catalysts." Org. Lett. (2006) 8(25) p. 5825-5828 + supporting information.*
Elkins, Jonathan M. et al; "Sttructure of factor inhibiting hypoxia inducible factor reveals mechanism of oxidative modification of hif-1alpha." J. Biol. Chem. (2003) 278(3) p. 1802-1806.*
Wang, Deyun et al; "Enhanced matobolic stability and protein binding properties of artificial alpha helices derived from a hydrogen bond surrogate: application of bcl-xl." Angew. Chem. Int. Ed. (2005) 44 p. 6525-6529.*
Elkins, Jonathan M. et al; "Sturcture of factor inhibiting hypoxia inducible factor reveals mechanism of oxidative modification of hif-1alpha." J. Biol. Chem. (2003) 278(3) p. 1802-1806.*
Chapman, Ross N. and Arora, Paramjit S.; "Optimized synthesis of hydrogen bond surrogate helices: surprising effects of microwave heating ont eh activity of grubbs catalysts." Org Lett (2006) 8(25) p. 5825-5828.*
Chapman, et al. Optimized synthesis of hydrogen-bond surrogate helices:? Surprising effects of microwave heating on the activity of Grubbs Catalysts. Organic Letters. 2006; 8(25):5825-5828.
European search report and opinion dated Feb. 9, 2012 for EP Application No. 09815315.8.
Henchey, et al. Contemporary strategies for the stabilization of peptides in the alpha-helical conformation. Current Opinion in Chemical Biology. 2008; 12(6):692-697.
Kung, et al. Suppression of tumor growth through disruption of hypoxia-inducible transcription. Nature Medicine. 2000; 6(12):1335-1340.

(Continued)

*Primary Examiner* — Maury Audet
*Assistant Examiner* — Fred Reynolds
(74) *Attorney, Agent, or Firm* — LeClairRyan, a Professional Corporation

(57) ABSTRACT

The present invention relates to peptides having one or more stable, internally constrained α-helices, and that include a sequence that mimics at least a portion of the C-terminal transactivation domain of HIF-1α. Also disclosed are pharmaceutical compositions containing these peptides and methods of using these peptides, for example to reduce gene transcription, treat or prevent disorders mediated by interaction of HIF-1α with CREB-binding protein and/or p300, reduce or prevent angiogenesis in a tissue, induce apoptosis, decrease cell survival and/or proliferation, and identify potential ligands of CREB-binding protein and/or p300.

6 Claims, 5 Drawing Sheets

(56) References Cited

OTHER PUBLICATIONS

Avantaggiati, M.L. Molecular horizons of cancer therapeutics: 11th Pezcoller symposium. Biochim Biophys Acta. May 17, 2000;1470(3):R49-59.

Freedman, et al. Structural basis for recruitment of CBP/p300 by hypoxia-inducible factor-1 alpha. Proc Natl Acad Sci U S A. Apr. 16, 2002;99(8):5367-72.

Henchey, et al. Inhibition of Hypoxia Inducible Factor 1—Transcription Coactivator Interaction by a Hydrogen Bond Surrogate α-Helix. J Am Chem Soc. Jan. 27, 2010;132(3):941-3.

International search report and written opinion dated May 18, 2010 for PCT Application No. US2009/057592.

Min, et al. Structure of an HIF-1alpha-pVHL complex: hydroxyproline recognition in signaling. Science. Jun. 7, 2002;296(5574):1886-9.

Chapman et al., "A Highly Stable Short α-Helix Constrained by a Main-Chain Hydrogen-Bond Surrogate," J. Am. Chem. Soc'y 126:12252-53 (2004).

Dames et al., "Structural Basis for HIF-1 α/CBP Recognition in the Cellular Hypoxic Response," Proc. Nat'l Acad. Sci. USA 99(8):5271-76 (2002).

Dimartino et al., "Solid-Phase Synthesis of Hydrogen-Bond Surrogate-Derived α-Helices," Org. Lett. 7(12):2389-92 (2005).

Hirota & Semenza, "Regulation of Angiogenesis by Hypoxia-Inducible Factor 1," Crit. Rev. Oncol./Hematol. 59:15-26 (2006).

International Application No. PCT/US2009/057592, International Preliminary Report on Patentability (Mar. 22, 2011).

Protein Databank No. 1L3E_A (Jul. 17, 2008).

Semenza, "Targeting HIF-1 for Cancer Therapy," Nat. Rev. Cancer 3:721-32 (2003).

Wang et al., "Evaluation of Biologically Relevant Short α-Helices Stabilized by a Main-Chain Hydrogen-Bond Surrogate," J. Am. Chem. Soc'y 128:9248-56 (2006).

Wang et al., "Nucleation and Stability of Hydrogen-Bond Surrogate-Based α-Helices," Org. Biomol. Chem. 4:4074-81 (2006).

Allen, "Long-Circulating (Sterically Stabilized) Liposomes for Targeted Drug Delivery," TiPS 15:215-20 (1994).

Almeida & Souto, "Solid Lipid Nanoparticles as a Drug Delivery System for Peptides and Proteins," Adv. Drug Deliv. Rev. 59:478-90 (2007).

Protein Data Bank Accession No. 1H2K, "Sequence" tab, at http://www.rcsb.org/explore.do?structured=1h2k (last accessed Feb. 20, 2014).

Sharma & Sharma, Review, "Liposomes in Drug Delivery: Progress and Limitations," Int'l J. Pharmaceut. 154:123-40 (1997).

Takeuchi et al., "Mucoadhesive Nanoparticulate Systems for Peptide Drug Delivery," Adv. Drug Deliv. Rev. 47:39-54 (2001).

Wender et al., "The Design, Synthesis, and Evaluation of Molecules That Enable or Enhance Cellular Uptake: Peptoid Molecular Transporters," Proc. Nat'l Acad. Sci. 97(24):13003-08 (2000).

\* cited by examiner

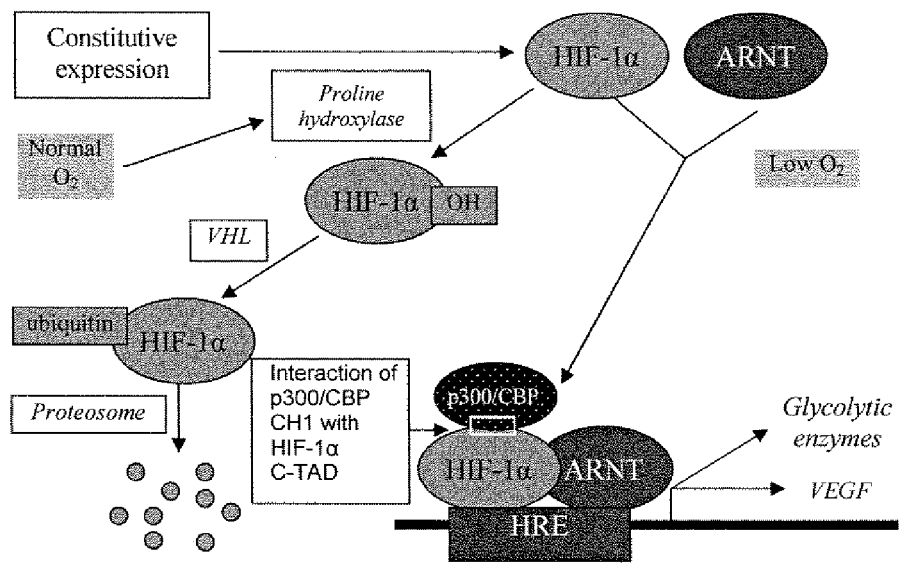
Figure 2
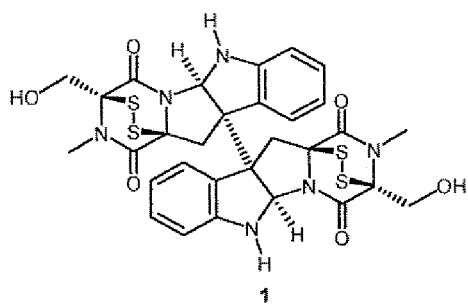 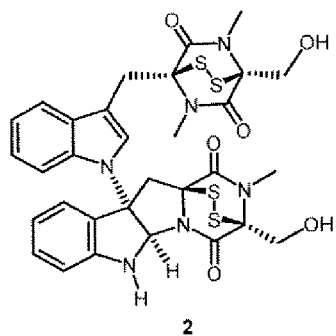
Figures 3A–B

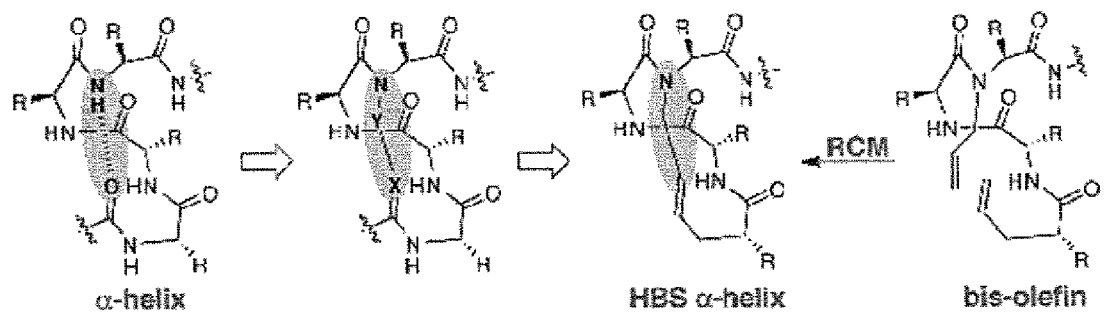
Figure 4
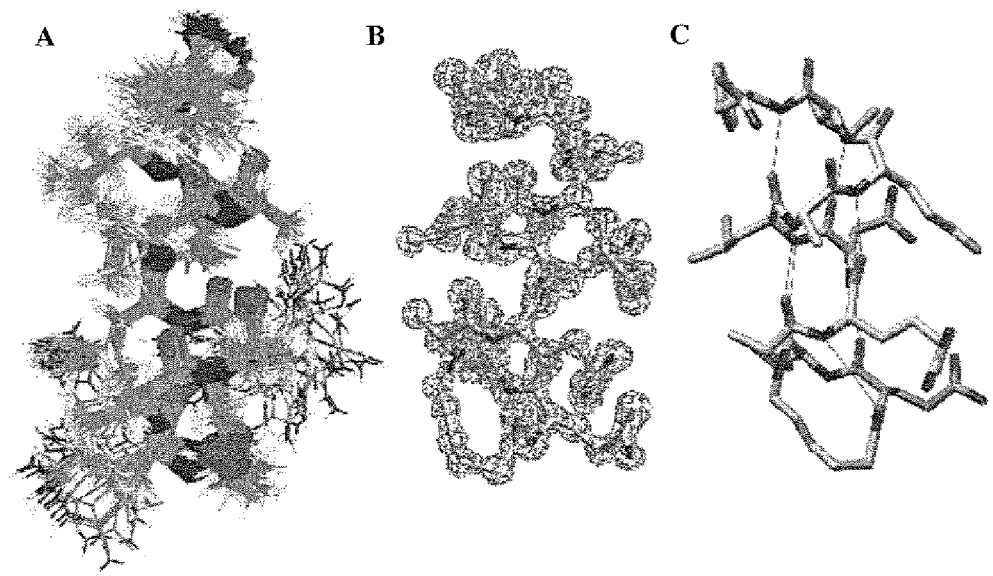
Figures 5A–C

SEQUENCE LISTING

```
<160> NUMBER OF SEQ ID NOS: 123

<210> SEQ ID NO 1
<211> LENGTH: 9
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (3)..(3)
<223> OTHER INFORMATION: Xaa at position 3 is N-allyltyrosine

<400> SEQUENCE: 1

Thr Ala Xaa Asp Cys Glu Val Asn Ala
1               5

<210> SEQ ID NO 2
<211> LENGTH: 9
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (3)..(3)
<223> OTHER INFORMATION: Xaa at position 3 is N-allyltyrosine

<400> SEQUENCE: 2

Thr Ala Xaa Asp Val Glu Val Asn Ala
1               5

<210> SEQ ID NO 3
<211> LENGTH: 10
<212> TYPE: PRT
<213> ORGANISM: Artificial
<220> FEATURE:
<223> OTHER INFORMATION: Hydrogen bond surrogate helix
<220> FEATURE:
```

```
<221> NAME/KEY: MISC_FEATURE
<222> LOCATION: (3)..(3)
<223> OTHER INFORMATION: Xaa at position 3 is N-allylalanine

<400> SEQUENCE: 3

Thr Ala Xaa Asp Cys Glu Tyr Asn Ala Arg
1               5                   10

<210> SEQ ID NO 4
<211> LENGTH: 10
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (3)..(3)
<223> OTHER INFORMATION: Xaa at position 3 is N-allyltyrosine

<400> SEQUENCE: 4

Thr Ala Xaa Asp Cys Glu Val Asn Ala Arg
1               5                   10

<210> SEQ ID NO 5
<211> LENGTH: 10
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (3)..(3)
<223> OTHER INFORMATION: Xaa at position 3 is N-allyltyrosine

<400> SEQUENCE: 5

Thr Ala Xaa Asp Cys Glu Val Arg Ala Arg
1               5                   10

<210> SEQ ID NO 6
<211> LENGTH: 10
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (3)..(3)
<223> OTHER INFORMATION: Xaa at position 3 is N-allylalanine

<400> SEQUENCE: 6

Thr Ala Xaa Asp Cys Glu Tyr Arg Ala Arg
1               5                   10

<210> SEQ ID NO 7
<211> LENGTH: 8
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (3)..(3)
<223> OTHER INFORMATION: Xaa at position 3 is N-allylleucine

<400> SEQUENCE: 7

Glu Glu Xaa Leu Arg Ala Leu Asp
1               5

<210> SEQ ID NO 8
```

<211> LENGTH: 41
<212> TYPE: PRT
<213> ORGANISM: Homo sapiens

<400> SEQUENCE: 8

Ser Met Asp Glu Ser Gly Leu Pro Gln Leu Thr Ser Tyr Asp Cys Glu
1               5                   10                  15

Val Asn Ala Pro Ile Gln Gly Ser Arg Asn Leu Leu Gln Gly Glu Glu
            20                  25                  30

Leu Leu Arg Ala Leu Asp Gln Val Asn
        35                  40

<210> SEQ ID NO 9
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 9

Asn Ala Gln Tyr Arg Ala
1               5

<210> SEQ ID NO 10
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 10

Asn Ala Gln Tyr Arg Ala Arg
1               5

<210> SEQ ID NO 11
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 11

Asn Ala Gln Tyr Asn Ala
1               5

<210> SEQ ID NO 12
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 12

Asn Ala Gln Tyr Asn Ala Arg
1               5

<210> SEQ ID NO 13
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 13

Asn Ala Gln Val Arg Ala
1               5

<210> SEQ ID NO 14
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 14

Asn Ala Gln Val Arg Ala Arg
1               5

<210> SEQ ID NO 15
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 15

Asn Ala Gln Val Asn Ala
1               5

<210> SEQ ID NO 16
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 16

Asn Ala Gln Val Asn Ala Arg
1               5

<210> SEQ ID NO 17
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 17

Asn Ala Glu Tyr Arg Ala
1               5

<210> SEQ ID NO 18
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 18

Asn Ala Glu Tyr Arg Ala Arg
1               5

<210> SEQ ID NO 19
<211> LENGTH: 6

```
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 19

Asn Ala Glu Tyr Asn Ala
1               5

<210> SEQ ID NO 20
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 20

Asn Ala Glu Tyr Asn Ala Arg
1               5

<210> SEQ ID NO 21
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 21

Asn Ala Glu Val Arg Ala
1               5

<210> SEQ ID NO 22
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 22

Asn Ala Glu Val Arg Ala Arg
1               5

<210> SEQ ID NO 23
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 23

Asn Ala Glu Val Asn Ala
1               5

<210> SEQ ID NO 24
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 24

Asn Ala Glu Val Asn Ala Arg
```

```
1               5

<210> SEQ ID NO 25
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 25

Asn Cys Gln Tyr Arg Ala
1               5

<210> SEQ ID NO 26
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 26

Asn Cys Gln Tyr Arg Ala Arg
1               5

<210> SEQ ID NO 27
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 27

Asn Cys Glu Tyr Asn Ala
1               5

<210> SEQ ID NO 28
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 28

Asn Cys Gln Tyr Asn Ala Arg
1               5

<210> SEQ ID NO 29
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 29

Asn Cys Gln Val Arg Ala
1               5

<210> SEQ ID NO 30
<211> LENGTH: 7
<212> TYPE: PRT
<213> ORGANISM: Artificial
<220> FEATURE:
<223> OTHER INFORMATION: Oligo peptide derived from the HIF-1alpha
``` c-terminal transactivation domain

<400> SEQUENCE: 30

Asn Cys Gln Val Arg Ala Arg
1               5

<210> SEQ ID NO 31
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 31

Asn Cys Gln Val Asn Ala
1               5

<210> SEQ ID NO 32
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 32

Asn Cys Gln Val Asn Ala Arg
1               5

<210> SEQ ID NO 33
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 33

Asn Cys Glu Tyr Arg Ala
1               5

<210> SEQ ID NO 34
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 34

Asn Cys Glu Tyr Arg Ala Arg
1               5

<210> SEQ ID NO 35
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 35

Asn Cys Glu Tyr Asn Ala
1               5

<210> SEQ ID NO 36

```
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 36

Asn Cys Glu Tyr Asn Ala Arg
1               5

<210> SEQ ID NO 37
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 37

Asn Cys Glu Val Arg Ala
1               5

<210> SEQ ID NO 38
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 38

Asn Cys Glu Val Arg Ala Arg
1               5

<210> SEQ ID NO 39
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 39

Asn Cys Glu Val Asn Ala
1               5

<210> SEQ ID NO 40
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 40

Asn Cys Glu Val Asn Ala Arg
1               5

<210> SEQ ID NO 41
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 41
```

Asn Val Gln Tyr Arg Ala
1               5

<210> SEQ ID NO 42
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 42

Asn Val Gln Tyr Arg Ala Arg
1               5

<210> SEQ ID NO 43
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 43

Asn Val Gln Tyr Asn Ala
1               5

<210> SEQ ID NO 44
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 44

Asn Val Gln Tyr Asn Ala Arg
1               5

<210> SEQ ID NO 45
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 45

Asn Val Gln Val Arg Ala
1               5

<210> SEQ ID NO 46
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 46

Asn Val Gln Val Arg Ala Arg
1               5

<210> SEQ ID NO 47
<211> LENGTH: 6
<212> TYPE: PRT
<213> ORGANISM: Artificial
<220> FEATURE:

```
<223> OTHER INFORMATION: Oligo peptide derived from the HIF-1alpha
      c-terminal transactivation domain

<400> SEQUENCE: 47

Asn Val Gln Val Asn Ala
1               5

<210> SEQ ID NO 48
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 48

Asn Val Gln Val Asn Ala Arg
1               5

<210> SEQ ID NO 49
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 49

Asn Val Glu Tyr Arg Ala
1               5

<210> SEQ ID NO 50
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 50

Asn Val Glu Tyr Arg Ala Arg
1               5

<210> SEQ ID NO 51
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 51

Asn Val Glu Tyr Asn Ala
1               5

<210> SEQ ID NO 52
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 52

Asn Val Glu Tyr Asn Ala Arg
1               5
```

```
<210> SEQ ID NO 53
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 53

Asn Val Glu Val Arg Ala
1               5

<210> SEQ ID NO 54
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 54

Asn Val Glu Val Arg Ala Arg
1               5

<210> SEQ ID NO 55
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 55

Asn Val Glu Val Asn Ala
1               5

<210> SEQ ID NO 56
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 56

Asn Val Glu Val Asn Ala Arg
1               5

<210> SEQ ID NO 57
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 57

Asp Ala Gln Tyr Arg Ala
1               5

<210> SEQ ID NO 58
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 58
```

Asp Ala Gln Tyr Arg Ala Arg
1               5

<210> SEQ ID NO 59
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 59

Asp Ala Gln Tyr Asn Ala
1               5

<210> SEQ ID NO 60
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 60

Asp Ala Gln Tyr Asn Ala Arg
1               5

<210> SEQ ID NO 61
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 61

Asp Ala Gln Val Arg Ala
1               5

<210> SEQ ID NO 62
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 62

Asp Ala Gln Val Arg Ala Arg
1               5

<210> SEQ ID NO 63
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 63

Asp Ala Gln Val Asn Ala
1               5

<210> SEQ ID NO 64
<211> LENGTH: 7
<212> TYPE: PRT
<213> ORGANISM: Artificial

```
<220> FEATURE:
<223> OTHER INFORMATION: Oligo peptide derived from the HIF-1alpha
      c-terminal transactivation domain

<400> SEQUENCE: 64

Asp Ala Gln Val Asn Ala Arg
1               5

<210> SEQ ID NO 65
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 65

Asp Ala Glu Tyr Arg Ala
1               5

<210> SEQ ID NO 66
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 66

Asp Ala Glu Tyr Arg Ala Arg
1               5

<210> SEQ ID NO 67
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 67

Asp Ala Glu Tyr Asn Ala
1               5

<210> SEQ ID NO 68
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 68

Asp Ala Glu Tyr Asn Ala Arg
1               5

<210> SEQ ID NO 69
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 69

Asp Ala Glu Val Arg Ala
1               5
```

<210> SEQ ID NO 70
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 70

Asp Ala Glu Val Arg Ala Arg
1               5

<210> SEQ ID NO 71
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 71

Asp Ala Glu Val Asn Ala
1               5

<210> SEQ ID NO 72
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 72

Asp Ala Glu Val Asn Ala Arg
1               5

<210> SEQ ID NO 73
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 73

Asp Cys Gln Tyr Arg Ala
1               5

<210> SEQ ID NO 74
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 74

Asp Cys Gln Tyr Arg Ala Arg
1               5

<210> SEQ ID NO 75
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

```
<400> SEQUENCE: 75

Asp Cys Gln Tyr Asn Ala
1               5

<210> SEQ ID NO 76
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 76

Asp Cys Gln Tyr Asn Ala Arg
1               5

<210> SEQ ID NO 77
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 77

Asp Cys Gln Val Arg Ala
1               5

<210> SEQ ID NO 78
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 78

Asp Cys Gln Val Arg Ala Arg
1               5

<210> SEQ ID NO 79
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 79

Asp Cys Gln Val Asn Ala
1               5

<210> SEQ ID NO 80
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 80

Asp Cys Gln Val Asn Ala Arg
1               5

<210> SEQ ID NO 81
<211> LENGTH: 6
<212> TYPE: PRT
```

```
<213> ORGANISM: Artificial
<220> FEATURE:
<223> OTHER INFORMATION: Oligo peptide derived from the HIF-1alpha
      c-terminal transactivation domain

<400> SEQUENCE: 81

Asp Cys Glu Tyr Arg Ala
1               5

<210> SEQ ID NO 82
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 82

Asp Cys Glu Tyr Arg Ala Arg
1               5

<210> SEQ ID NO 83
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 83

Asp Cys Glu Tyr Asn Ala
1               5

<210> SEQ ID NO 84
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 84

Asp Cys Glu Tyr Asn Ala Arg
1               5

<210> SEQ ID NO 85
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 85

Asp Cys Glu Val Arg Ala
1               5

<210> SEQ ID NO 86
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 86

Asp Cys Glu Val Arg Ala Arg
1               5
```

```
<210> SEQ ID NO 87
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 87

Asp Cys Glu Val Asn Ala
1               5

<210> SEQ ID NO 88
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 88

Asp Cys Glu Val Asn Ala Arg
1               5

<210> SEQ ID NO 89
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 89

Asp Val Gln Tyr Arg Ala
1               5

<210> SEQ ID NO 90
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 90

Asp Val Gln Tyr Arg Ala Arg
1               5

<210> SEQ ID NO 91
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 91

Asp Val Gln Tyr Asn Ala
1               5

<210> SEQ ID NO 92
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain
```

```
<400> SEQUENCE: 92

Asp Val Gln Tyr Asn Ala Arg
1               5

<210> SEQ ID NO 93
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 93

Asp Val Gln Val Arg Ala
1               5

<210> SEQ ID NO 94
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 94

Asp Val Gln Val Arg Ala Arg
1               5

<210> SEQ ID NO 95
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 95

Asp Val Gln Val Asn Ala
1               5

<210> SEQ ID NO 96
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 96

Asp Val Gln Val Asn Ala Arg
1               5

<210> SEQ ID NO 97
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 97

Asp Val Glu Tyr Arg Ala
1               5

<210> SEQ ID NO 98
<211> LENGTH: 7
```

```
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 98

Asp Val Glu Tyr Arg Ala Arg
1               5

<210> SEQ ID NO 99
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 99

Asp Val Glu Tyr Asn Ala
1               5

<210> SEQ ID NO 100
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 100

Asp Val Glu Tyr Asn Ala Arg
1               5

<210> SEQ ID NO 101
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 101

Asp Val Glu Val Arg Ala
1               5

<210> SEQ ID NO 102
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 102

Asp Val Glu Val Arg Ala Arg
1               5

<210> SEQ ID NO 103
<211> LENGTH: 6
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 103

Asp Val Glu Val Asn Ala
```

<210> SEQ ID NO 104
<211> LENGTH: 7
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 104

Asp Val Glu Val Asn Ala Arg
1               5

<210> SEQ ID NO 105
<211> LENGTH: 20
<212> TYPE: DNA
<213> ORGANISM: Artificial
<220> FEATURE:
<223> OTHER INFORMATION: Forward primer for VEGF

<400> SEQUENCE: 105
aggccagcac ataggagaga                                                 20

<210> SEQ ID NO 106
<211> LENGTH: 20
<212> TYPE: DNA
<213> ORGANISM: Artificial
<220> FEATURE:
<223> OTHER INFORMATION: Reverse primer for VEGF

<400> SEQUENCE: 106
tttccctttc ctcgaactga                                                 20

<210> SEQ ID NO 107
<211> LENGTH: 22
<212> TYPE: DNA
<213> ORGANISM: Artificial
<220> FEATURE:
<223> OTHER INFORMATION: Forward primer for GLUT1

<400> SEQUENCE: 107
tagaaacatg gttttgaaat gc                                              22

<210> SEQ ID NO 108
<211> LENGTH: 22
<212> TYPE: DNA
<213> ORGANISM: Artificial
<220> FEATURE:
<223> OTHER INFORMATION: Reverse primer for GLUT1

<400> SEQUENCE: 108
ggtaacaggg atcaaacaga tt                                              22

<210> SEQ ID NO 109
<211> LENGTH: 22
<212> TYPE: DNA
<213> ORGANISM: Artificial
<220> FEATURE:
<223> OTHER INFORMATION: Forward primer for Beta-glucuronidase

<400> SEQUENCE: 109
ctcatttgga attttgccga tt                                              22

<210> SEQ ID NO 110
<211> LENGTH: 22

```
<212> TYPE: DNA
<213> ORGANISM: Artificial
<220> FEATURE:
<223> OTHER INFORMATION: Reverse primer for Beta-glucuronidase

<400> SEQUENCE: 110
ccgagtgaag atcccctttt ta                                              22

<210> SEQ ID NO 111
<211> LENGTH: 9
<212> TYPE: PRT
<213> ORGANISM: Homo sapiens

<400> SEQUENCE: 111

Ser Tyr Asp Cys Glu Val Asn Ala Pro
1               5

<210> SEQ ID NO 112
<211> LENGTH: 10
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allyltyrosine

<400> SEQUENCE: 112

Xaa Thr Ala Xaa Asp Cys Glu Val Asn Ala
1               5                   10

<210> SEQ ID NO 113
<211> LENGTH: 10
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allyltyrosine

<400> SEQUENCE: 113

Xaa Thr Ala Xaa Asp Val Glu Val Asn Ala
1               5                   10

<210> SEQ ID NO 114
<211> LENGTH: 11
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allylalanine

<400> SEQUENCE: 114
```

Xaa Thr Ala Xaa Asp Cys Glu Tyr Asn Ala Arg
1               5                   10

<210> SEQ ID NO 115
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: position 1 is acetylated

<400> SEQUENCE: 115

Thr Ser Tyr Asp Cys Glu Val Asn Ala
1               5

<210> SEQ ID NO 116
<211> LENGTH: 9
<212> TYPE: PRT
<213> ORGANISM: Artificial
<220> FEATURE:
<223> OTHER INFORMATION: Oligo peptide derived from the HIF-1alpha
      c-terminal transactivation domain
<220> FEATURE:
<221> NAME/KEY: MISC_FEATURE
<222> LOCATION: (1)..(1)
<223> OTHER INFORMATION: position 1 is acetylated

<400> SEQUENCE: 116

Thr Ala Tyr Asp Cys Glu Val Asn Ala
1               5

<210> SEQ ID NO 117
<211> LENGTH: 11
<212> TYPE: PRT
<213> ORGANISM: Artificial
<220> FEATURE:
<223> OTHER INFORMATION: Oligo peptide derived from the HIF-1alpha
      c-terminal transactivation domain
<220> FEATURE:
<221> NAME/KEY: MISC_FEATURE
<222> LOCATION: (1)..(1)
<223> OTHER INFORMATION: position 1 is acetylated

<400> SEQUENCE: 117

Gly Thr Ala Ala Asp Cys Glu Tyr Asn Ala Arg
1               5                   10

<210> SEQ ID NO 118
<211> LENGTH: 11
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allyltyrosine

<400> SEQUENCE: 118

Xaa Thr Ala Xaa Asp Cys Glu Val Asn Ala Arg
1               5                   10

<210> SEQ ID NO 119
<211> LENGTH: 11

-continued

```
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allyltyrosine

<400> SEQUENCE: 119

Xaa Thr Ala Xaa Asp Cys Glu Val Arg Ala Arg
1               5                   10

<210> SEQ ID NO 120
<211> LENGTH: 11
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allylalanine

<400> SEQUENCE: 120

Xaa Thr Ala Xaa Asp Cys Glu Tyr Arg Ala Arg
1               5                   10

<210> SEQ ID NO 121
<211> LENGTH: 12
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allylalanine
<220> FEATURE:
<221> NAME/KEY: MISC_FEATURE
<222> LOCATION: (12)..(12)
<223> OTHER INFORMATION: position 12 is labeled with a fluorescent
      marker

<400> SEQUENCE: 121

Xaa Thr Ala Xaa Asp Cys Glu Tyr Asn Ala Arg Lys
1               5                   10

<210> SEQ ID NO 122
<211> LENGTH: 9
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
```

```
<223> OTHER INFORMATION: Xaa at position 4 is N-allylleucine

<400> SEQUENCE: 122

Xaa Glu Glu Xaa Leu Arg Ala Leu Asp
1               5

<210> SEQ ID NO 123
<211> LENGTH: 10
<212> TYPE: PRT
<213> ORGANISM: Artificial
<220> FEATURE:
<223> OTHER INFORMATION: Oligo peptide derived from the HIF-1alpha
      c-terminal transactivation domain

<400> SEQUENCE: 123

Thr Ala Ala Asp Cys Glu Tyr Asn Ala Arg
1               5                   10
```

INHIBITING INTERACTION BETWEEN THE HIF-1ALPHA AND P300/CBP WITH HYDROGEN BOND SURROGATE-BASED HELICES

CROSS-REFERENCE

This application is the national phase entry under 35 U.S.C. 371 of PCT/US2009/057592, filed Sep. 18, 2009, which claims the benefit under 35 U.S.C. 119(e) of U.S. Provisional Application No. 61/098,193, filed Sep. 18, 2008, which application is incorporated herein by reference.

STATEMENT AS TO FEDERALLY SPONSORED RESEARCH

This invention was made with government support under grant numbers GM073943, awarded by the National Institutes of Health. The government has certain rights in this invention.

BACKGROUND OF THE INVENTION

The Role of HIF-1α-Coactivator Interactions in Regulation of VEGF Transcription

The interaction between the cysteine-histidine rich 1 domain ("CH1") of the coactivator protein p300 (or the homologous CREB binding protein, CBP) and the C-terminal transactivation domain ("C-TAD," aa 786-826 of NCBI accession number NP 001521) of the hypoxia-inducible factor 1α ("HIF-1α") (Freedman et al., "Structural Basis for Recruitment of CBP/p300 by Hypoxia-inducible Factor-1α," Proc. Nat'l Acad. Sci. USA 99:5367-72 (2002); Dames et al., "Structural Basis for HIF-1α/CBP Recognition in the Cellular Hypoxic Response," Proc. Nat'l Acad. Sci. USA 99:5271-6 (2002)) mediates transactivation of hypoxia-inducible genes (Hirota & Semenza, "Regulation of Angiogenesis by Hypoxia-inducible Factor 1," Crit. Rev. Oncol. Hematol. 59:15-26 (2006); Semenza, "Targeting HIF-1 for Cancer Therapy," Nat. Rev. Cancer 3:721-32 (2003)). Hypoxia-inducible genes are important contributors in angiogenesis and cancer metastasis, as shown in FIGS. 1A-C (Orourke et al., "Identification of Hypoxically Inducible mRNAs in HeLa Cells Using Differential-display PCR," Eu. J. Biochem. 241: 403-10 (1996); Ivan et al., "HIFα Targeted for VHL-mediated Destruction by Proline Hydroxylation: Implications for $O_2$Sensing," Science 292:464-8 (2001)). Under normoxia, the α-subunit of HIF-1 is successively hydroxylated at proline residues 402 and 564 by proline hydroxylases, ubiquitinated, and then degraded by the ubiquitin-proteosome system, as shown in FIG. 2. This process, mediated by the von Hippel-Lindau tumor suppressor protein (Kaelin, "Molecular Basis of the VHL Hereditary Cancer Syndrome," Nat. Rev. Cancer 2:673-82 (2002)), is responsible for controlling levels of HIF-1α and, as a result, the transcriptional response to hypoxia (Maxwell et al., "The Tumour Suppressor Protein VHL Targets Hypoxia-inducible Factors for Oxygen-dependent Proteolysis," Nature 399:271-5 (1999)). Under hypoxic conditions, HIF-1α is no longer targeted for destruction and accumulates. Heterodimerization with its constitutively expressed binding partner, aryl hydrocarbon receptor nuclear translocator ("ARNT") (Wood et al., "The Role of the Aryl Hydrocarbon Receptor Nuclear Translocator (ARNT) in Hypoxic Induction of Gene Expression," J. Biol. Chem. 271: 15117-23 (1996)) results in binding to a cognate hypoxia response element ("HRE") (Forsythe et al., "Activation of Vascular Endothelial Growth Factor Gene Transcription by Hypoxia-inducible Factor 1," Mol. Cell. Biol. 16:4604-13 (1996)). A third site of regulatory hydroxylation on Asparagine 803 is also inhibited under hypoxic conditions (Lando et al., "FIH-I is an Asparaginyl Hydroxylase Enzyme That Regulates the Transcriptional Activity of Hypoxia-inducible Factor," Genes & Develop. 16:1466-71 (2002)), allowing recruitment of the p300/CBP coactivators, which trigger overexpression of hypoxia inducible genes, as shown in FIG. 2. Among these are genes encoding angiogenic peptides such as vascular endothelial growth factor ("VEGF") and VEGF receptors VEGFR-I (Flt-1) and VEGFR-2 (KDR/Flk-1), as well as proteins involved in altered energy metabolism, such as the glucose transporters GLUT1 and GLUT3, and hexokinases 1 and 2 (Forsythe et al., "Activation of Vascular Endothelial Growth Factor Gene Transcription by Hypoxia-inducible Factor 1," Mol. Cell. Biol. 16:4604-13 (1996); Okino et al., "Hypoxia-inducible Mammalian Gene Expression Analyzed in Vivo at a TATA-driven Promoter and at an Initiator-driven Promoter," J. Biol. Chem. 273:23837-43 (1998)).

Epidithiodiketopiperazine Fungal Metabolites as Regulators of Hypoxia-inducible Transcription Because interaction of HIF-1α C-TAD with transcriptional coactivator p300/CBP is a point of significant amplification in transcriptional response, its disruption with designed protein ligands could be an effective means of suppressing aerobic glycolysis and angiogenesis (i.e., the formation of new blood vessels) in cancers (Hirota & Semenza, "Regulation of Angiogenesis by Hypoxia-inducible Factor 1," Crit. Rev. Oncol. Hematol. 59:15-26 (2006); Ramanathan et al., "Perturbational Profiling of a Cell-line Model of Tumorigenesis by Using Metabolic Measurements," Proc. Nat'l Acad. Sci. USA 102:5992-7 (2005); Underiner et al., "Development of Vascular Endothelial Growth Factor Receptor (VEGFR) Kinase Inhibitors as Anti-angiogenic Agents in Cancer Therapy," Curr. Med. Chem. 11:73145 (2004)). Although the contact surface of the HIF-1α C-TAD with p300/CBP is extensive (3393 Å$^2$) the inhibition of this protein-protein interaction may not require direct interference. Instead, the induction of a structural change to one of the binding partners (p300/CBP) may be sufficient to disrupt the complex (Kung et al., "Small Molecule Blockade of Transcriptional Coactivation of the Hypoxia-inducible Factor Pathway," Cancer Cell 6:33-43 (2004)).

Although inhibition of nuclear protein-protein interactions with small molecules in the past has proven to be difficult (Arkin & Wells, "Small-molecule Inhibitors of Protein-Protein Interactions: Progressing Towards the Dream," Nat. Rev. Drug Discov. 3:301-17 (2004)), recent screens for high-affinity protein ligands have resulted in several remarkable accomplishments (Kung et al., "Small Molecule Blockade of Transcriptional Coactivation of the Hypoxia-inducible Factor Pathway," Cancer Cell 6:33-43 (2004); Issaeva et al., "Small Molecule RITA Binds to p53, Blocks p53-HDM-2 Interaction and Activates p53 Function in Tumors," Nat. Med. 10: 1321-8 (2004); Lepourcelet et al., "Small-molecule Antagonists of the Oncogenic Tcf/β-Catenin Protein Complex," Cancer Cell 5:91-102 (2004); Vassilev et al., "In Vivo Activation of the p53 Pathway by Small-molecule Antagonists of MDM2," Science 303:844-8 (2004); Grasberger et al., "Discovery and Cocrystal Structure of Benzodiazepinedione HDM2 Antagonists That Activate p53 in Cells," J. Med. Chem. 48:909-12 (2005); Ding et al., "Structure-based Design of Potent Non-peptide MDM2 Inhibitors," J. Am. Chem. Soc. 127:10130-1 (2005); Berg et al., "Small-molecule Antagonists of Myc/Max Dimerization Inhibit Myc-induced Transformation of Chicken Embryo Fibroblasts," Proc. Nat'l Acad. Sci. USA 99:3830-5 (2002); International Patent Publication No. WO 2006/066775 to De Munari et al.). Two small molecules, chaetocin 1 (Hauser et al., "Isolation and Structure Elucidation of Chaetocin," Hely. Chirn. Acta 53(5):1061-73 (1970)) (shown in FIG. 3A) and chetomin 2 (Waksman & Bugie, "Chaetomin, a New Antibiotic Substance Produced by Chaetomium Cochliodes I. Formation and Properties," J. Bacteriol. 48:527-30 (1944)) (shown in FIG. 3B), have been shown to inhibit the interaction between HIF-1α C-TAD and p300/CBP and to attenuate hypoxia-inducible transcription, although the exact mechanism of this inhibition remains unclear (Kung et al., "Small Molecule Blockade of Transcriptional Coactivation of the Hypoxia-inducible Factor Pathway," Cancer Cell 6:33-43 (2004)). Despite the initial encouraging reports, further design of inhibitors of the HIF-1 pathway is needed, because both 1 and 2 have induced coagulative necrosis, anemia, and leukocytosis in experimental animals. It would be desirable to identify other inhibitors of the HIF-1 pathway that lack or have diminished side effects.

The present invention is directed to overcoming these and other deficiencies in the art.

SUMMARY OF THE INVENTION

In one aspect, the invention provides a peptide having one or more stable, internally-constrained α-helices, wherein the peptide comprises a sequence that mimics helix αA or helix αB of the C-terminal transactivation domain of Hypoxia-Inducible Factor 1α. In one embodiment, the peptide is a peptide of formula I:

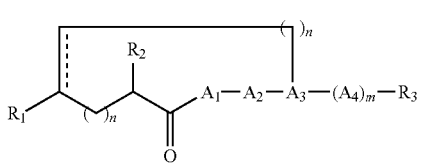

(I)

wherein

===== is a single or double carbon-carbon bond, where the double carbon-carbon bond is cis or trans;

each n is independently 1 or 2;

m is zero or any positive integer;

$R_1$ is an amino acid, a peptide, —$OR_4$, —$CH_2NH_2$, an alkyl group, an aryl group, or hydrogen, wherein $R_4$ is alkyl or aryl;

or $R_1$ has the formula:

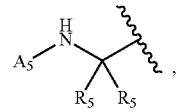

wherein $A_5$ is a peptide, an amino acid residue, an acyl group, or hydrogen; and
each $R_5$ is independently an amino acid side chain, hydrogen, an alkyl, or an aryl group;

$R_2$ is hydrogen, an amino acid side chain, an alkyl group, or an aryl group;

$R_3$ is an amino acid, a peptide, —$OR_6$, —$N(R_7)_2$, an alkyl group, an aryl group, or hydrogen, wherein $R_6$ is an alkyl group or an aryl group and each $R_7$ is independently an amino acid side chain, hydrogen, an alkyl group, or an aryl group;

$A_1$, $A_2$ and $A_4$ are each independently:

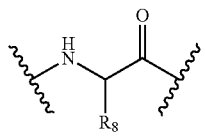

wherein each $R_8$ is hydrogen, an amino acid side chain, an alkyl group, or an aryl group; and
$A_3$ is

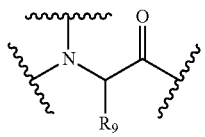

wherein each $R_9$ is hydrogen, an amino acid side chain, an alkyl group, or an aryl group.

The peptide according to claim 2, wherein
(i) $A_1$ is Thr; $A_2$ is Ser or Ala; $A_3$ is Tyr or Ala; and $A_4$ comprises the formula $X^1X^2X^3X^4X^5X^6X^7$, wherein $X^1$ is Asp or Asn, $X^2$ is Val, Cys, or Ala, $X^3$ is Glu or Gln, $X^4$ is Val or Tyr, $X^5$ is Asn or Arg, $X^6$ is Ala, and $X^7$ is Arg or absent; or
(ii) $A_1$ and $A_2$ are independently Glu or Gln; $A_3$ is Leu; and $A_4$ comprises the formula $LRX^8LX^9$, where L is Leu, R is Arg, $X^8$ is Ala or Tyr, and $X^9$ is Asp or Asn.

In another embodiment, the peptide is selected from the group consisting of:

(SEQ ID NO: 1)

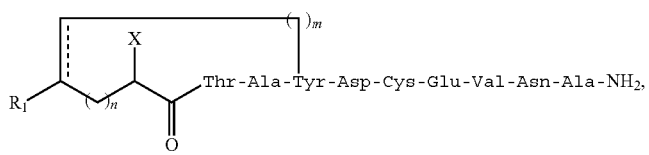

(SEQ ID NO: 2)

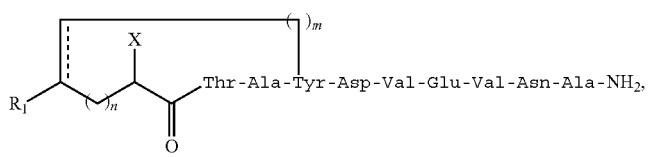

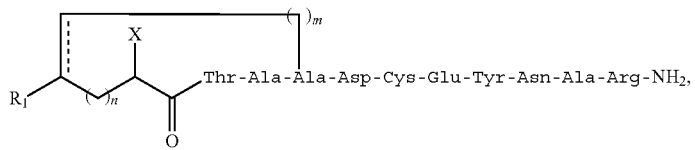

(SEQ ID NO: 3)
Thr-Ala-Ala-Asp-Cys-Glu-Tyr-Asn-Ala-Arg-NH₂,

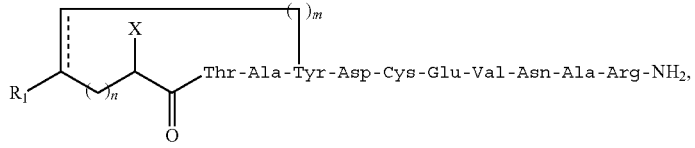

(SEQ ID NO: 4)
Thr-Ala-Tyr-Asp-Cys-Glu-Val-Asn-Ala-Arg-NH₂,

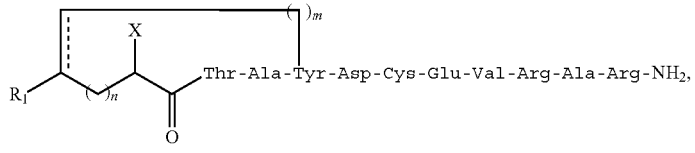

(SEQ ID NO: 5)
Thr-Ala-Tyr-Asp-Cys-Glu-Val-Arg-Ala-Arg-NH₂,

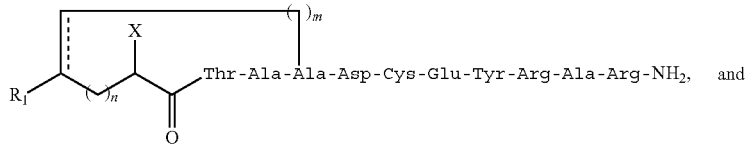

(SEQ ID NO: 6)
Thr-Ala-Ala-Asp-Cys-Glu-Tyr-Arg-Ala-Arg-NH₂, and

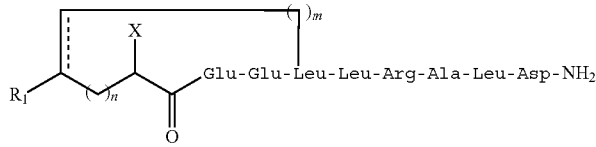

(SEQ ID NO: 7)
Glu-Glu-Leu-Leu-Arg-Ala-Leu-Asp-NH₂ wherein m and n are independently 1 or 2; and
X is hydrogen, an amino acid side chain, an alkyl group, or an aryl group.

In one embodiment, m and n are 1. In another embodiment, m is 1 and n is 2. In another embodiment, m is 2 and n is 1. In yet another embodiment, both m and n are 2.

In some embodiments, a peptide of the invention peptide mimics at least residues 796-804 or residues 816-823 of the C-terminal transactivation domain of Hypoxia-inducible Factor 1α.

In another aspect, the invention also provides a pharmaceutical composition comprising a peptide of the invention and a pharmaceutically acceptable vehicle.

In yet another aspect, the invention provides a method of reducing transcription of a gene in a cell, wherein transcription of the gene is mediated by interaction of Hypoxia-Inducible Factor 1α with CREB-binding protein and/or p300, said method comprising contacting the cell with a peptide according to claim 1 under conditions effective to reduce transcription of the gene. In some embodiments, the gene is selected from the group consisting of adenylate kinase 3, aldolase A, aldolase C, enolase 1, glucose transporter 1, glucose transporter 3, glyceraldehyde-3-phosphate dehydrogenase, hexokinase 1, hexokinase 2, insulin-like growth factor 2, IGF binding protein 1, IGF binding protein 3, lactate dehydrogenase A, phosphoglycerate kinase 1, pyruvate kinase M, p21, transforming growth factor $_{β3}$, ceruloplasmin, erythropoietin, transferrin, transferrin receptor, $_{α1B}$-adrenergic receptor, adrenomedullin, endothelin-1, heme oxygenase 1, nitric oxide synthase 2, plasminogen activator inhibitor 1, vascular endothelial growth factor, vascular endothelial growth factor receptor FLT-1, vascular endothelial growth factor receptor KDR/Flk-1, and p3$^{5srg}$.

Also provided is a method of treating or preventing in a subject in need thereof a disorder mediated by interaction of Hypoxia-inducible Factor 1α with CREB-binding protein and/or p300, said method comprising administering to the subject a peptide of the invention under conditions effective to treat or prevent the disorder. In some embodiments, the disorder is selected from the group consisting of retinal ischemia, pulmonary hypertension, intrauterine growth retardation, diabetic retinopathy, age-related macular degeneration, diabetic macular edema, and cancer.

In another aspect, the invention relates to a method of reducing or preventing angiogenesis in a tissue, said method comprising contacting the tissue with a peptide of the invention under conditions effective to reduce or prevent angiogenesis in the tissue. In some embodiments, the method is carried out in vivo. In other embodiments, the tissue is a tumor.

The invention further provides a method of inducing apoptosis in a cell, said method comprising contacting the cell with a peptide of the invention under conditions effective to induce apoptosis of the cell. The invention also provides a method of decreasing survival and/or proliferation of a cell, said method comprising contacting the cell with a peptide of the invention under conditions effective to decrease survival and/or proliferation of the cell. In some embodiments, the cell is cancerous or is contained in the endothelial vasculature of a tissue that contains cancerous cells. In another aspect, the invention relates to a method of identifying a potential ligand of CREB-binding protein and/or p300, said method comprising: providing a peptide of the invention, contacting the peptide with a test agent, and detecting whether the test agent selectively binds to the peptide, wherein a test agent that selectively binds to the peptide is identified as a potential ligand of CREB-binding protein and/or p300.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 is a schematic diagram illustrating the HIF-1α pathway. ARNT represents the aryl hydrocarbon receptor nuclear translocator; VHL represents the von Hippel-Lindau tumor suppressor; HRE represents the hypoxia response element; and VEGF represents vascular endothelial growth factor.

FIGS. 3A-B are schematic diagrams showing the structures of chaetocin 1 (isolated from Chaetomium globosum) (FIG. 3A) and chetomin 2 (isolated from Chaetomium codiodes) (FIG. 3B).

FIG. 4 is a schematic diagram illustrating the nucleation of short α-helices by replacement of an N-terminal i and i+4 hydrogen bond (C=O—H—N) with a covalent link (C=X—Y—N). These hydrogen bond surrogate-based ("HBS") α-helices contain a carbon-carbon bond derived from a ring-closing metathesis reaction ("RCM").

FIGS. 5A-C are schematic illustrations of the structure of an HBS α-helix. FIG. 5A shows the NMR-derived structure of an HBS α-helix. FIG. 5B shows an X-ray crystallography-derived 1.1 Å resolution electron density map of an HBS α-helix with the refined molecular model. FIG. 5C shows the molecular model of an HBS α-helix from crystallographic data. The narrow lines depict putative i and i+4 hydrogen bonds.

FIG. 6A depicts its chemical structure. FIG. 6B shows the circular dichroism spectra of HBS helix 22 and control peptide 25 in 10 mM of phosphate buffer at pH 7.4.

DETAILED DESCRIPTION OF THE INVENTION

Figure 1A:
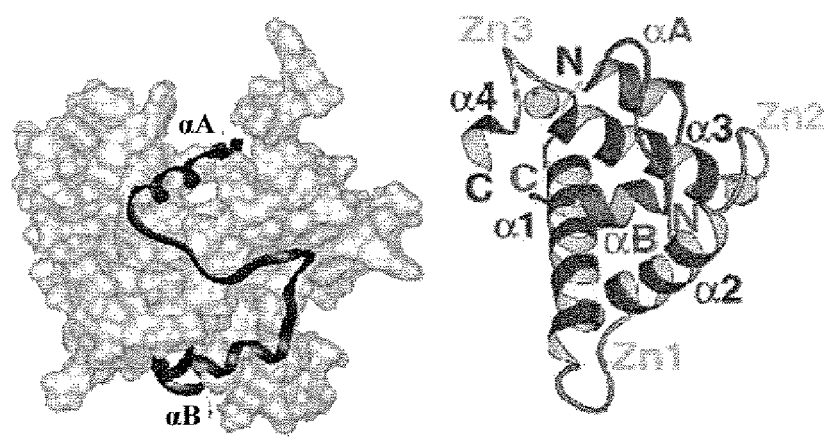
FIG. 1A is a schematic diagram illustrating the structure of the complex of the C-terminal transactivation domain ("C-TAD") of the hypoxia-inducible factor 1a ("HIF-1α") with cysteine-histidine rich 1 domain ("CH1") of the coactivator protein p300 (or the homologous CREB binding protein, CBP) (Lepourcelet et al., "Small-molecule Antagonists of the Oncogenic Tcf/fβ-Catenin Protein Complex," Cancer Cell 5:91-102 (2004); Vassilev et al., "In Vivo Activation of the p53 Pathway by Small-molecule Antagonists of MDM2," Science 303:844-8 (2004).
Figure 1B:
FIG. 1B illustrates the domain map of HIF-1α showing the basic helix-loop-helix region ("bHLH"), PAS, the N-terminal transactivation domain ("N-TAD"), and the C-TAD. The human HIF-1α C-TAD sequence (SEQ ID NO: 8) is shown in FIG. 1C, along with the location of the αA and αB helices.

Design of α-Helical Compounds of the Invention

In one aspect, the present invention relates to hydrogen bond surrogate ("HBS") α-helices that modulate the interaction between HIF-1α C-TAD and the p300/CBP CH1 domain.

Peptides composed of less than 15 amino acid residues do not generally form α-helical structures at physiological conditions once excised from the protein environment, and require artificial constraints to adopt α-helical conformation. HIF-1α features two short α-helical regions composed of eight amino acid residues each. The HIF-1α/coactivator interface was targeted with hydrogen bond surrogate ("HBS") derived α-helices with the goal of reproducibly producing stable helical structures from short peptide sequences, as shown in FIG. 4 (Wang et al., "Evaluation of Biologically Relevant Short α-Helices Stabilized by a Main-chain Hydrogen-bond Surrogate," J. Am. Chem. Soc. 128:9248-56 (2006), which is hereby incorporated by reference in its entirety). Although other approaches for the design of helix mimetics have been described in the literature, often these methods require "belts and braces" to stabilize the conformation. The HBS approach uniquely allows synthesis of α-helices with all faces available for molecular recognition, because side chain functionality is not utilized to lock the conformation.

The HBS helix design approach is centered on the helix-coil transition theory, which suggests that the energetically demanding organization of three consecutive amino acids into the helical orientation inherently limits the stability of short α-helices (Lifson & Roig, "On the Theory of Helix-Coil Transitions in Polypeptides," J. Chem. Phys. 34:1963-74 (1961); Zimm & Bragg, "Theory of the Phase Transition Between Helix and Random Coil in Polypeptide Chains," J. Chem. Phys. 31:526-35 (1959), which are hereby incorporated by reference in their entirety). According to this theory, α-helices composed often or fewer amino acids are expected to be essentially unstable due to a low nucleation probability. The HBS approach affords a pre-organized a-turn to overcome the intrinsic nucleation barrier and to initiate helix formation. In an α-helix, a hydrogen bond between the C=O of the $i^{th}$ amino acid residue and the NH of the $i+4^{th}$ amino acid residue stabilizes and nucleates the helical structure, as shown in FIG. 4. To mimic the C=O—H—N hydrogen bond as closely as possible, and to pre-organize the α-turn, a covalent bond of the type C=X—Y—N is utilized, where X and Y are part of the i and the i+4 residues, respectively. This method is envisioned as being broadly applicable to prepare any structurally c constrained αhelix. Similar methods may be used to prepare structurally constrained In one embodiment, the covalent bond between the i and the i+4 residues is a carbon-carbon bond derived from a ring-closing metathesis reaction (Chapman et al., "A Highly Stable Short α-Helix Constrained by a Main-chain Hydrogen-bond Surrogate," J. Am. Chem. Soc. 126:12252-3 (2004); Dimartino et al., "Solid-phase Synthesis of Hydrogen-bond Surrogate-derived α-Helices," Org. Lett. 7:2389-92 (2005), which are hereby incorporated by reference in their entirety).

NMR-derived solution structure and high resolution crystal structure of HBS α-helices unequivocally illustrate the potential of this approach, as shown in FIG. 5 (Wang et al., "Evaluation of Biologically Relevant Short α-Helices Stabilized by a Main-chain Hydrogen-bond Surrogate," J. Am. Chem. Soc. 128:9248-56 (2006); Liu et al., "Atomic Structure of a Short Alpha-helix Stabilized by a Main Chain Hydrogen Bond Surrogate," J. Am. Chem. Soc. 130:4334-7 (2008), which are hereby incorporated by reference in their entirety). Two features of the HBS approach make it especially attractive for the design of allosteric transcriptional regulators: (1) the internal placement of the crosslink, which allows for the design of α-helices without blocking solvent-exposed surfaces and thereby preserving side chains for molecular recognition, and (2) the ability to constrain very short peptides with less than 10 amino acid residues into highly stable α-helices (Wang et al., "Evaluation of Biologically Relevant Short α-Helices Stabilized by a Main-chain Hydrogen-bond Surrogate," J. Am. Chem. Soc. 128:9248-56 (2006); Wang et al., "Nucleation and Stability of Hydrogen-bond Surrogate-based α-Helices," Org. Biomol. Chem. 4:4074-81 (2006), which are hereby incorporated by reference in their entirety).

A first aspect of the present invention relates to a peptide having one or more stable, internally-constrained alpha-helices, where the peptide includes a sequence that mimics a portion of a HIF-1α helical domain. In one embodiment, the HIF-1α helical domain is helix αA or helix αB of the C-terminal transactivation domain of HIF-1α. For example, the peptide mimics at least residues 796-804 or residues 816-823 of the HIF-1α C-terminal transactivation domain.

Suitable peptides of the invention include peptides of the formula I:

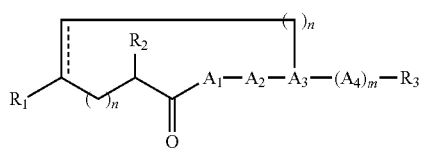

(I)

wherein ≡≡≡ is a single or double carbon-carbon bond, where the double carbon-carbon bond is cis or trans; each n is independently 1 or 2; and m is zero or any positive integer. For example, m may be any integer from 3 to 16, or 3 to 40. $R_1$ may be an amino acid, a peptide, $-OR_4$, $-CH_2NH_2$, an alkyl group, an aryl group, or hydrogen, wherein $R_4$ is alkyl or aryl. Alternatively, $R_1$ is a moiety of the formula:

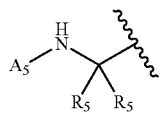

wherein $A_5$ is an amino acid residue, an acyl group, or hydrogen; and each $R_5$ is independently an amino acid side chain, hydrogen, an alkyl, or an aryl group. $R_2$ may be hydrogen, an amino acid side chain, an alkyl group, or an aryl group. $R_3$ may be an amino acid, a peptide, $-OR_6$, $-N(R_7)_2$, an alkyl group, an aryl group, or hydrogen, wherein $R_6$ is an alkyl group or an aryl group and each $R_7$ is independently an amino acid side chain, hydrogen, an alkyl group, or an aryl group. $A_1$, $A_2$ and $A_4$ are each independently:

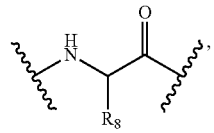

wherein each $R_8$ is hydrogen, an amino acid side chain, an alkyl group, or an aryl group; and $A_3$ is:

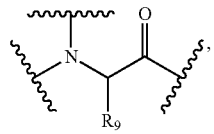

wherein each $R_9$ is hydrogen, an amino acid side chain, an alkyl group, or an aryl group.

Amino acids useful in practicing the invention include natural and unnatural amino acids, disubstituted amino acids, beta-amino acids, gamma-amino acids, and others, and residues referred to herein include residues obtained from such amino acids. In one embodiment, amino acid side chains referred to in compounds of the invention, such as Formula I, are natural amino acid side chains.

"Alkyl group" as used herein is a linear or branched chain alkyl group. Also included within the definition of alkyl are heteroalkyl groups, wherein the heteroatom can be nitrogen, oxygen, phosphorus, sulfur and silicon. Alkyl groups include, but are not limited to, methyl, ethyl, propyl, isopropyl, and butyl. Alkyl groups include, for example, C1-C6 alkyls.

"Acyl group" as used herein includes linear or branched chain acyl groups, such as methanoyl, ethanoyl, propanoyl, benzoyl, and propenoyl.

"Aryl group" as used herein includes aromatic aryl rings such as phenyl, heterocyclic aromatic rings such as pyridine, furan, thiophene, pyrrole, indole and purine, and heterocyclic rings with nitrogen, oxygen, sulfur or phosphorus.

Included in the definition of alkyl, acyl, and aryl groups are substituted alkyl, acyl, and aryl groups. Suitable substitution groups include but are not limited to, halogens, amines, hydroxyl groups, carboxylic acids, nitro groups, carbonyl, and other alkyl, acyl, and aryl groups.

Peptides that mimic helix αA of the C-terminal transactivation domain of HIF-1α include, without limitation, those of formula I where $A_1$ is Thr; $A_2$ is Ser or Ala; $A_3$ is Tyr or Ala; and $A_4$ comprises the formula $X^1X^2X^3X^4X^5X^6X^7$, wherein $X^1$ is Asp or Asn, $X^2$ is Val, Cys, or Ala, $X^3$ is Glu or Gln, $X^4$ is Val or Tyr, $X^5$ is Asn or Arg, $X^6$ is Ala, and $X^7$ is Arg or absent. As will be understood by the skilled artisan, $A_4$ can be selected from the group of Asn-Ala-Gln-Tyr-Arg-Ala (SEQ ID NO:9), Asn-Ala-Gln-Tyr-Arg-Ala-Arg (SEQ ID NO:10), Asn-Ala-Gln-Tyr-Asn-Ala (SEQ ID NO:11), Asn-Ala-Gln-Tyr-Asn-Ala-Arg (SEQ ID NO:12), Asn-Ala-Gln-Val-Arg-Ala (SEQ ID NO:13), Asn-Ala-Gln-Val-Arg-Ala-Arg (SEQ ID NO:14), Asn-Ala-Gln-Val-Asn-Ala (SEQ ID NO:15), Asn-Ala-Gln-Val-Asn-Ala-Arg (SEQ ID NO:16), Asn-Ala-Glu-Tyr-Arg-Ala (SEQ ID NO:17), Asn-Ala-Glu-Tyr-Arg-Ala-Arg (SEQ ID NO:18), Asn-Ala-Glu-Tyr-Asn-Ala (SEQ ID NO:19), Asn-Ala-Glu-Tyr-Asn-Ala-Arg (SEQ ID NO:20), Asn-Ala-Glu-Val-Arg-Ala (SEQ ID NO:21), Asn- Ala-Glu-Val-Arg-Ala-Arg (SEQ ID NO:22), Asn-Ala-Glu-Val-Asn-Ala (SEQ ID NO:23), Asn-Ala-Glu-Val-Asn-Ala-Arg (SEQ ID NO:24), Asn-Cys-Gln-Tyr-Arg-Ala (SEQ ID NO:25), Asn-Cys-Gln-Tyr-Arg-Ala-Arg (SEQ ID NO:26), Asn-Cys-Glu-Tyr-Asn-Ala (SEQ ID NO:27), Asn-Cys-Gln-Tyr-Asn-Ala-Arg (SEQ ID NO:28), Asn-Cys-Gln-Val-Arg-Ala (SEQ ID NO:29), Asn-Cys-Gln-Val-Arg-Ala-Arg (SEQ ID NO:30), Asn-Cys-Gln-Val-Asn-Ala (SEQ ID NO:31), Asn-Cys-Gln-Val-Asn-Ala-Arg (SEQ ID NO:32), Asn-Cys-Glu-Tyr-Arg-Ala (SEQ ID NO:33), Asn-Cys-Glu-Tyr-Arg-Ala-Arg (SEQ ID NO:34), Asn-Cys-Glu-Tyr-Asn-Ala (SEQ ID NO:35), Asn-Cys-Glu-Tyr-Asn-Ala-Arg (SEQ ID NO:36), Asn-Cys-Glu-Val-Arg-Ala (SEQ ID NO:37), Asn-Cys-Glu-Val-Arg-Ala-Arg (SEQ ID NO:38), Asn-Cys-Glu-Val-Asn-Ala (SEQ ID NO:39), Asn-Cys-Glu-Val-Asn-Ala-Arg (SEQ ID NO:40), Asn-Val-Gln-Tyr-Arg-Ala (SEQ ID NO:41), Asn-Val-Gln-Tyr-Arg-Ala-Arg (SEQ ID NO:42), Asn-Val-Gln-Tyr-Asn-Ala (SEQ ID NO:43), Asn-Val-Gln-Tyr-Asn-Ala-Arg (SEQ ID NO:44), Asn-Val-Gln-Val-Arg-Ala (SEQ ID NO:45), Asn-Val-Gln-Val-Arg-Ala-Arg (SEQ ID NO:46), Asn-Val-Gln-Val-Asn-Ala (SEQ ID NO:47), Asn-Val-Gln-Val-Asn-Ala-Arg (SEQ ID NO:48), Asn-Val-Glu-Tyr-Arg-Ala (SEQ ID NO:49), Asn-Val-Glu-Tyr-Arg-Ala-Arg (SEQ ID NO:50), Asn-Val-Glu-Tyr-Asn-Ala (SEQ ID NO:51), Asn-Val-Glu-Tyr-Asn-Ala-Arg (SEQ ID NO:52), Asn-Val-Glu-Val-Arg-Ala (SEQ ID NO:53), Asn-Val-Glu-Val-Arg-Ala-Arg (SEQ ID NO:54), Asn-Val-Glu-Val-Asn-Ala (SEQ ID NO:55), Asn-Val-Glu-Val-Asn-Ala-Arg (SEQ ID NO:56), Asp-Ala-Gln-Tyr-Arg-Ala (SEQ ID NO:57), Asp-Ala-Gln-Tyr-Arg-Ala-Arg (SEQ ID NO:58), Asp-Ala-Gln-Tyr-Asn-Ala (SEQ ID NO:59), Asp-Ala-Gln-Tyr-Asn-Ala-Arg (SEQ ID NO:60), Asp-Ala-Gln-Val-Arg-Ala (SEQ ID NO:61), Asp-Ala-Gln-Val-Arg-Ala-Arg (SEQ ID NO:62), Asp-Ala-Gln-Val-Asn-Ala (SEQ ID NO:63), Asp-Ala-Gln-Val-Asn-Ala-Arg (SEQ ID NO:64), Asp-Ala-Glu-Tyr-Arg-Ala (SEQ ID NO:65), Asp-Ala-Glu-Tyr-Arg-Ala-Arg (SEQ ID NO:66), Asp-Ala-Glu-Tyr-Asn-Ala (SEQ ID NO:67), Asp-Ala-Glu-Tyr-Asn-Ala-Arg (SEQ ID NO:68), Asp-Ala-Glu-Val-Arg-Ala (SEQ ID NO:69), Asp-Ala-Glu-Val-Arg-Ala-Arg (SEQ ID NO:70), Asp-Ala-Glu-Val-Asn-Ala (SEQ ID NO:71), Asp-Ala-Glu-Val-Asn-Ala-Arg (SEQ ID NO:72), Asp-Cys-Gln-Tyr-Arg-Ala (SEQ ID NO:73), Asp-Cys-Gln-Tyr-Arg-Ala-Arg (SEQ ID NO:74), Asp-Cys-Gln-Tyr-Asn-Ala (SEQ ID NO:75), Asp-Cys-Gln-Tyr-Asn-Ala-Arg (SEQ ID NO:76), Asp-Cys-Gln-Val-Arg-Ala (SEQ ID NO:77), Asp-Cys-Gln-Val-Arg-Ala-Arg (SEQ ID NO:78), Asp-Cys-Gln-Val-Asn-Ala (SEQ ID NO:79), Asp-Cys-Gln-Val-Asn-Ala-Arg (SEQ ID NO:80), Asp-Cys-Glu-Tyr-Arg-Ala (SEQ ID NO:81), Asp-Cys-Glu-Tyr-Arg-Ala-Arg (SEQ ID NO:82), Asp-Cys-Glu-Tyr-Asn-Ala (SEQ ID NO:83), Asp-Cys-Glu-Tyr-Asn-Ala-Arg (SEQ ID NO:84), Asp-Cys-Glu-Val-Arg-Ala (SEQ ID NO:85), Asp-Cys-Glu-Val-Arg-Ala-Arg (SEQ ID NO:86), Asp-Cys-Glu-Val-Asn-Ala (SEQ ID NO:87), Asp-Cys-Glu-Val-Asn-Ala-Arg (SEQ ID NO:88), Asp-Val-Gln-Tyr-Arg-Ala (SEQ ID NO:89), Asp-Val-Gln-Tyr-Arg-Ala-Arg (SEQ ID NO:90), Asp-Val-Gln-Tyr-Asn-Ala (SEQ ID NO:91), Asp-Val-Gln-Tyr-Asn-Ala-Arg (SEQ ID NO:92), Asp-Val-Gln-Val-Arg-Ala (SEQ ID NO:93), Asp-Val-Gln-Val-Arg-Ala-Arg (SEQ ID NO:94), Asp-Val-Gln-Val-Asn-Ala (SEQ ID NO:95), Asp-Val-Gln-Val-Asn-Ala-Arg (SEQ ID NO:96), Asp-Val-Glu-Tyr-Arg-Ala (SEQ ID NO:97), Asp-Val-Glu-Tyr-Arg-Ala-Arg (SEQ ID NO:98), Asp-Val-Glu-Tyr-Asn-Ala (SEQ ID NO:99), Asp-Val-Glu-Tyr-Asn-Ala-Arg (SEQ ID NO:100), Asp-Val-Glu-Val-Arg-Ala (SEQ ID NO:101), Asp-Val-Glu-Val-Arg-Ala-Arg (SEQ ID NO:102), Asp-Val-Glu-Val-Asn-Ala (SEQ ID NO:103), and Asp-Val-Glu-Val-Asn-Ala-Arg (SEQ ID NO: 104). Exemplary peptides include:

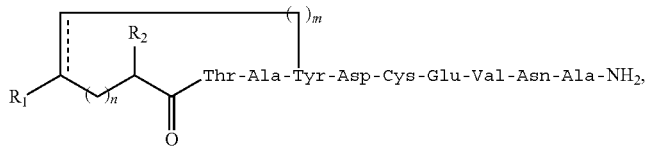

(SEQ ID NO: 1)

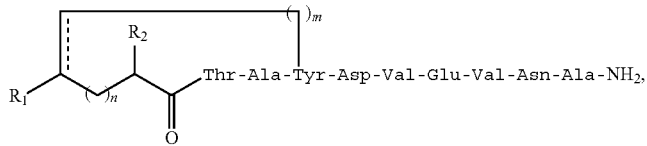

(SEQ ID NO: 2)

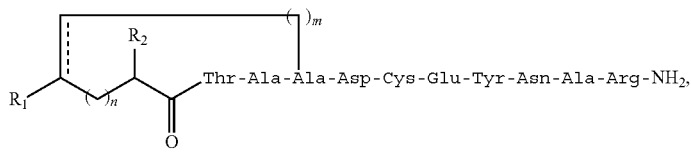

(SEQ ID NO: 3)

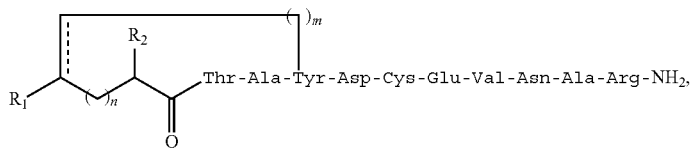

(SEQ ID NO: 4)

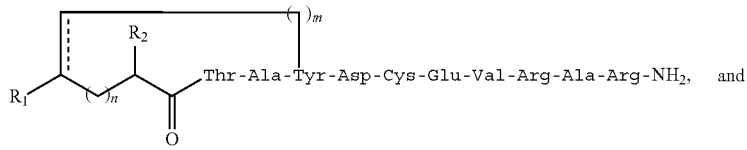
Thr-Ala-Tyr-Asp-Cys-Glu-Val-Arg-Ala-Arg-NH$_2$, and (SEQ ID NO: 5)

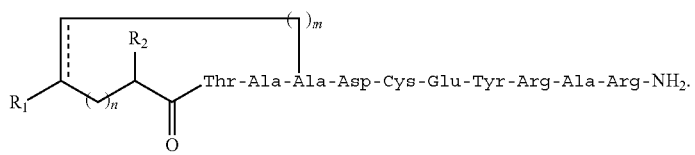
Thr-Ala-Ala-Asp-Cys-Glu-Tyr-Arg-Ala-Arg-NH$_2$. (SEQ ID NO: 6)

In the peptides shown directly above, m and n are independently 1 or 2. For example, each of m and n may be 1. Alternatively, m is 1 and n is 2. In another embodiment, m is 2 and n is 1. In yet another embodiment, both m and n are 2.

Generally, suitable peptides of the present invention include those that include the formula:

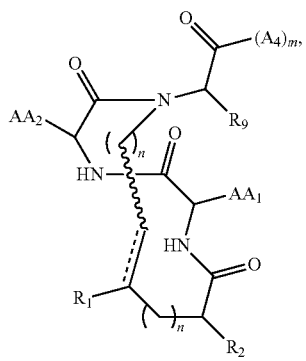

where

===== is a single or double carbon-carbon bond;

∼∼∼ is a single bond and is cis or trans when ===== is a double bond;

each n is independently 1 or 2; m is any integer;

$R_1$ is an amino acid, peptide, —$OR_4$, —$CH_2NH_2$, an alkyl group, an aryl group, hydrogen, or a group having a formula

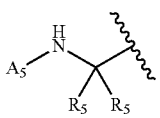

wherein $A_5$ is a peptide, an amino acid residue, an acyl group, or hydrogen; and each $R_5$ is independently an amino acid side chain, hydrogen, an alkyl, or an aryl group;

$R_2$ is hydrogen, an amino acid side chain, an alkyl group, or an aryl group;

$AA_1$ and $AA_2$ are independently an amino acid side chain, an alkyl group, or an aryl group; and $A_4$ is as defined above for Formula I.

In one embodiment, $R_1$ is hydrogen. In another embodiment, $R_1$ is

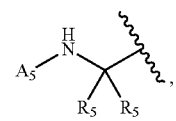

where $A_5$ is a peptide connected through a peptide bond.

In one embodiment, the bond represented by ===== is a single bond. In another embodiment, the bond represented by ===== is a double bond.

In other embodiments, the methods of the present invention may be used to prepare peptides having highly stabilized, internally-constrained α-helices. The constraint may be placed anywhere within the peptide, not just at the N-terminus. For example, a compound prepared according to the methods of the present invention may have the formula

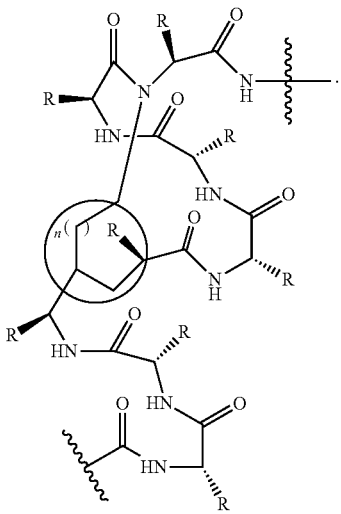

constraint in the middle
n = 1, 2

In the above formula, each R is independently any amino acid side chain

The peptides produced according to the methods of the present invention may, for example, be less than 50, 45, 40, 35, 30, 25, 20, 15, or less than 10 amino acid residues. In one embodiment, the peptides of the invention are less than 50 amino acid long.

HBS α-helices of the present invention may be prepared, for example, by replacing an N-terminal main-chain i and i+4 hydrogen bond with a carbon-carbon bond through a ring-closing metathesis reaction, as shown in FIG. 2 (U.S. Pat. No. 7,202,332 to Arora et al.; Chapman & Arora, "Optimized Synthesis of Hydrogen-bond Surrogate Helices: Surprising Effects of Microwave Heating on the Activity of Grubbs Catalysts," *Org. Lett.* 8:5825-8 (2006); Chapman et al., "A Highly Stable Short α-Helix Constrained by a Main-chain Hydrogen-bond Surrogate," *J. Am. Chem. Soc.* 126:12252-3 (2004); Dimartino et al., "Solid-phase Synthesis of Hydrogen-bond Surrogate-derived α-Helices," *Org. Lett.* 7:2389-92 (2005), which are hereby incorporated by reference in their entirety). The hydrogen bond surrogate pre-organizes an α-turn and stabilizes the peptide sequence in an α-helical conformation. HBS α-helices have been shown to adopt stable α-helical conformations from a variety of short peptide sequences (Wang et al., "Evaluation of Biologically Relevant Short α-Helices Stabilized by a Main-chain Hydrogen-bond Surrogate," *J. Am. Chem. Soc.* 128:9248-56 (2006), which is hereby incorporated by reference in its entirety). It has also been shown that these artificial α-helices can target their expected protein receptor with high affinity (Wang et al., "Enhanced Metabolic Stability and Protein-binding Properties of Artificial α Helices Derived from a Hydrogen-bond Surrogate: Application to Bcl-xL," *Angew. Chem. Int'l Ed. Engl.* 44:6525-9 (2005), originally published at *Angew. Chem.* 117:6683-7 (2005), which is hereby incorporated by reference in its entirety). For example, preparing a compound of the invention involves providing a peptide precursor compound and promoting carbon-carbon bond formation to result in a stable, internally-constrained alpha-helix.

In one embodiment, the precursor has the formula:

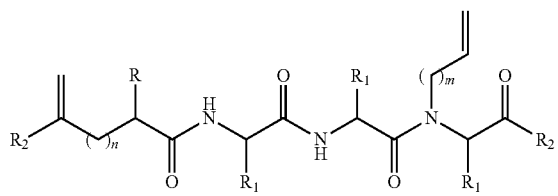

The compound of the formula above may be reacted under conditions effective to promote formation of a carbon-carbon bond. Such a reaction may be, for example, metathesis. The exceptional functional group tolerance displayed by the olefin metathesis catalysts for the facile introduction of non-native carbon-carbon constraints in the preparation of peptidomimetics suggests that X and Y could be two carbon atoms connected through an olefin metathesis reaction, as shown in Scheme 2 (Hoveyda et al., "Ru Complexes Bearing Bidentate Carbenes: From Innocent Curiosity to Uniquely Effective Catalysts for Olefin Metathesis," *Org. Biomolec. Chem.* 2:8-23 (2004); Trnka et al., "The Development of L2X2Tu=CHR Olefin Metathesis Catalysts: An Organometallic Success Story," *Accounts Chem. Res.* 34:18-29 (2001), which are hereby incorporated by reference in their entirety).

This aspect of the present invention may, for example, involve a ring-closing olefin metathesis reaction. An olefin metathesis reaction couples two double bonds (olefins) to afford two new double bonds (one of which is typically ethylene gas). A ring-closing olefin metathesis utilizes an olefin metathesis reaction to form a macrocycle. In this reaction, two double bonds within a chain are connected. The reaction may be performed with a metathesis catalyst, for example of the formula

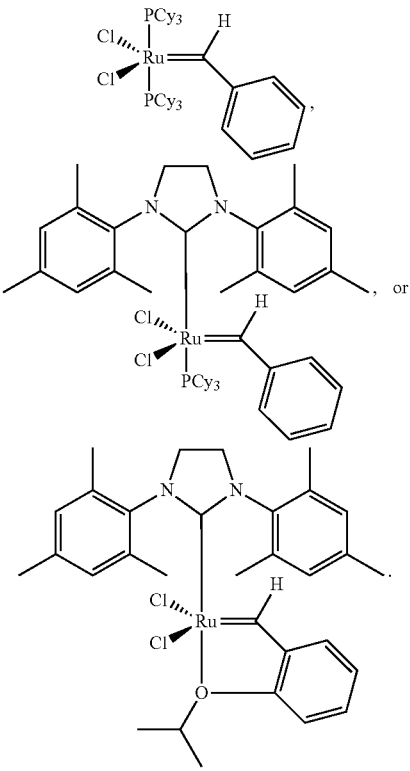

In other embodiments, the metathesis catalyst is of the formula

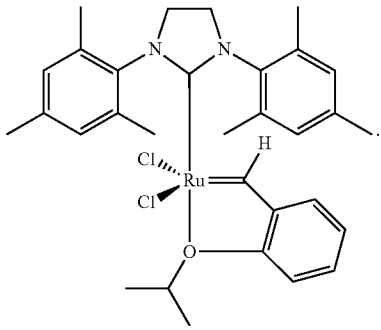

The metathesis reaction may be performed, for example, at a temperature between about 25° C. and 110° C., and more preferably, at a temperature of about 50° C.

The metathesis reaction may be performed with an organic solvent, such as dichloromethane, dichloroethane, trichloroethane, or toluene.

The reactions disclosed herein may, for example, be carried out on a solid support. Suitable solid supports include particles, strands, precipitates, gels, sheets, tubing, spheres, containers, capillaries, pads, slices, films, plates, slides, discs, membranes, etc. These solid supports can be made from a wide variety of materials, including polymers, plastics, ceramics, polysaccharides, silica or silica-based materials, carbon, metals, inorganic glasses, membranes, or composites thereof. The substrate is preferably flat but may take on a variety of alternative surface configurations. For example, the substrate may contain raised or depressed regions on which the synthesis takes place. The substrate and its surface preferably form a rigid support on which to carry out the reactions described herein. Other substrate materials will be readily apparent to those of ordinary skill in the art upon review of this disclosure.

The metathesis reaction performed may initially yield a compound in which the newly formed carbon-carbon bond is a double bond. This double bond can be subsequently converted to a single bond by hydrogenation methods known in the art.

Also encompassed by the present invention is a pharmaceutical composition that includes a peptide of the present invention and a pharmaceutically acceptable vehicle.

As will be apparent to one of ordinary skill in the art, administering may be carried out using generally known methods. Administration can be accomplished either via systemic administration to the subject or via targeted administration to affected cells. Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, by application to mucous membranes (such as that of the nose, throat, bronchial tubes, genitals, and/or anus), or implantation of a sustained release vehicle.

The peptide of the present invention will be administered to a mammal as a pharmaceutical formulation that includes the therapeutic agent and any pharmaceutically acceptable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers and/or excipients. The amount of active compound in such therapeutically useful compositions is such that a suitable dosage unit will be obtained.

The agents may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

The peptides of the invention may also be administered parenterally. Solutions or suspensions of the peptides can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The peptides according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The peptides of the present invention may be administered directly to a targeted tissue, e.g., tissue that is susceptible to infection by the virus. Additionally and/or alternatively, the agent may be administered to a non-targeted area along with one or more agents that facilitate migration of the agent to (and/or uptake by) a targeted tissue, organ, or cell. While the targeted tissue can be any tissue subject to infection by the virus, preferred target tissues in the case of inhibiting HIV-1 infection include mucous membranes of the mouth, genitals, and rectum. As will be apparent to one of ordinary skill in the art, the therapeutic agent itself be modified to facilitate its transport to (and uptake by) the desired tissue, organ, or cell.

Exemplary delivery devices include, without limitation, nebulizers, atomizers, liposomes, transdermal patches, implants, implantable or injectable protein depot compositions, and syringes. Other delivery systems which are known to those of skill in the art can also be employed to achieve the desired delivery of the therapeutic agent to the desired organ, tissue, or cells in vivo to effect this aspect of the present invention.

Any suitable approach for delivery of the peptides can be utilized to practice this aspect of the present invention. Typically, the peptides will be administered to a patient in a vehicle that delivers the peptides to the target cell, tissue, or organ.

One approach for delivering peptides into cells involves the use of liposomes. Generally, this involves providing a liposome which includes agent(s) to be delivered, and then contacting the target cell, tissue, or organ with the liposomes under conditions effective for delivery of the agent into the cell, tissue, or organ.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner where the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987), which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., each of which is hereby incorporated by reference in its entirety.

These liposomes can be produced such that they contain, in addition to the therapeutic agents of the present invention, other therapeutic agents, such as anti-inflammatory agents, which would then be released at the target site (e.g., Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), which is hereby incorporated by reference in its entirety).

An alternative approach for delivery of proteins or polypeptide agents (e.g., peptides of the present invention) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins according to U.S. Pat. No. 5,817,789 to Heartlein et al., which is hereby incorporated by reference in its entirety. The chimeric protein can include a ligand domain and the polypeptide agent (e.g., the artificial α-helix of the present invention). The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein.

Administration can be carried out as frequently as required and for a duration that is suitable to provide effective treatment against viral infection. For example, administration can be carried out with a single sustained-release dosage formulation or with multiple daily doses. Administration can be carried out before, concurrently with, and/or after exposure of the subject to the virus.

The amount to be administered will, of course, vary depending upon the treatment regimen. Generally, an agent is administered to achieve an amount effective for a reduction in infectivity of the virus (i.e., a therapeutically effective amount). Thus, a therapeutically effective amount can be an amount which is capable of at least partially preventing transmission of the virus to the subject, or spread of the virus within the subject. The dose required to obtain an effective amount may vary depending on the agent, formulation, virus, and individual to whom the agent is administered.

Determination of effective amounts may also involve in vitro assays in which varying doses of agent are administered to cells in culture and the concentration of agent effective for inhibiting infectivity is determined in order to calculate the concentration required in vivo. Effective amounts may also be based on in vivo animal studies. A therapeutically effective amount can be determined empirically by those of skill in the art.

A second aspect of the present invention relates to inhibiting the HIF 1α-p300/CBP interaction using the peptides of the present invention. One embodiment of this aspect of the present invention relates to a method of reducing transcription of a gene in a cell, where transcription of the gene is mediated by interaction of HIF-1α with CREB-binding protein and/or p300. This method involves contacting the cell with a peptide of the present invention under conditions effective to cause nuclear uptake of the peptide, where the peptide disrupts interaction of HIF-1α and p300/CBP and thereby reduces transcription of the gene. Genes whose transcription is mediated by interaction of HIF-1α with CBP and/or p300 include adenylate kinase 3, aldolase A, aldolase C, enolase 1, glucose transporter 1, glucose transporter 3, glyceraldehyde-3-phosphate dehydrogenase, hexokinase 1, hexokinase 2, insulin-like growth factor 2, IGF binding protein 1, IGF binding protein 3, lactate dehydrogenase A, phosphoglycerate kinase 1, pyruvate kinase M, p21, transforming growth factor $\beta_3$, ceruloplasmin, erythropoietin, transferrin, transferrin receptor, a1B-adrenergic receptor, adrenomedullin, endothelin-1, heme oxygenase 1, nitric oxide synthase 2, plasminogen activator inhibitor 1, vascular endothelial growth factor, vascular endothelial growth factor receptor FLT-1, vascular endothelial growth factor receptor KDR/Flk-1, and $p35^{srg}$. Some uses for inhibiting transcription of these genes are shown in Table 1.

TABLE 1

Example disorders.

| Gene | Disease to treat/prevent |
| --- | --- |
| Enolase 1 | Hashimoto's encelopathy, severe asthma |
| Glucose transporter 1 | Aerobic glycolysis (Warburg effect) |
| Glucose transporter 3 | Aerobic glycolysis (Warburg effect) |
| Hexokinase 1 | Aerobic glycolysis (Warburg effect) |
| Hexokinase 2 | Aerobic glycolysis (Warburg effect) |
| Insulin-like growth factor 2 | Abnormal development and function of organs (brain, liver) |
| IGF binding protein 1 | Abnormal development and function of organs (brain, liver) |
| IGF binding protein 3 | Abnormal development and function of organs (brain, liver) |
| Lactate dehydrogenase A | Myocardial infarction |
| Ceruloplasmin | Lymphoma, acute and chronic inflammation, rheumatoid arthritis |
| Erythropoietin | Abnormal oxygen transport |
| Transferrin | Abnormal iron uptake/metabolism |
| Transferrin receptor | Abnormal iron uptake/metabolism |
| Adrenomedullin | Pheochromocytoma |
| Endothelin-1 | Abnormal vasoconstriction |
| Heme oxygenase 1 | Abnormal oxygen transport |
| Nitric oxide synthase 2 | Abnormal vasomotor tone |
| Vascular endothelial growth factor | Angiogenesis (tumors, including cancer) |
| Vascular endothelial growth factor receptor FLT-1 | Angiogenesis (tumors, including cancer) |
| Vascular endothelial growth factor receptor KDR/Flk-1 | Angiogenesis (tumors, including cancer) |

Another embodiment of this aspect of the present invention relates to a method of treating or preventing in a subject in need thereof a disorder mediated by interaction of HIF-1α with CBP and/or p300. This method involves administering a peptide of the present invention to the subject under conditions effective to treat or prevent the disorder.

Disorders that can be treated or prevented include, for example, retinal ischemia (Zhu et al., "Long-term Tolerance to Retinal Ischemia by Repetitive Hypoxic Preconditioning: Role of HIF-1α and Heme Oxygenase-1," Invest. Ophthalmol. Vis. Sci. 48: 1735-43 (2007); Ding et al., "Retinal Disease in Mice. Lacking Hypoxia-inducible Transcription Factor-2α," Invest. Ophthalmol. Vis. Sci. 46:1010-6 (2005), each of which is hereby incorporated by reference in its entirety), pulmonary hypertension (Simon et al., "Hypoxia-induced Signaling in the Cardiovascular System," Annu. Rev. Physiol. 70:51-71 (2008); Eul et al., "Impact of HIF-1α and HIF-2α on Proliferatiou and Migration of Human Pulmonary Artery Fibroblasts in Hypoxia," FASEB J. 20:163-5 (2006), each of which is hereby incorporated by reference jn its entirety), intrauterine growth retardation (Caramelo et al., "Respuesta a la Hipoxia. Un Mecanismo Sistemico Basado en el Control de la Expresion Genica [Response to Hypoxia. A Systemic Mechanism Based on the Control of Gene Expression]," Medicina B. Aires 66: 155-{54 (2006); Tazuke et al., "Hypoxia Stimulates Insulin-like Growth Factor Binding Protein I (IGFBP-1) Gene Expression in HepG2 Cells: A Possible Model for IGFBP-1 Expression in Fetal Hypoxia," Proc. Nat'l Acad. Sci. USA 95:10188-93 (1998), each of which is hereby incorporated by reference in its entirety), diabetic retinopathy (Ritter et al., "Myeloid Progenitors Differentiate into Microglia and Promote Vascular Repair in a Model of Ischemic Retinopathy," J. Clin Invest. 116:3266-76 (2006); Wilkinson-Berka et al., "The Role of Growth Hormone, Insulin-like Growth Factor and Somatostatin in Diabetic Retinopathy," Curr. Med. Chem. 13:3307-17 (2006); Vinores et al., "Implication of the Hypoxia Response Element of the Vegf Promoter in Mouse Models of Retinal and Choroidal Neovascularization, but Not Retinal Vascular Development," J. Cell. Physiol. 206:749-58 (2006); Caldwell et al., "Vascular Endothelial Growth Factor and Diabetic Retinopathy: Role of Oxidative Stress," Curr. Drug Targets 6:511-24 (2005), each of which is hereby incorporated by reference in its entirety), age-related macular degeneration (Inoue et al., "Expression of Hypoxia-inducible Factor 1a and 2a in Choroidal Neovascular Membranes Associated with Age-related Macular Degeneration," Br. J. Ophthalmol. 91:1720-1 (2007); Zuluaga et al., "Synergies of VEGF Inhibition and Photodynamic Therapy in the Treatment of Age-related Macular Degeneration," Invest. Ophthalmol. Vis. Sci 48:1767-72 (2007); Provis, "Development of the Primate Retinal Vasculature," Prog. Retin Eye Res. 20:799-821 (2001), each of which is hereby incorporated by reference in its entirety), diabetic macular edema (Vinores et al., "Implication of the Hypoxia Response Element of the Vegf Promoter in Mouse Models of Retinal and Choroidal Neovascularization, but Not Retinal Vascular Development," J. Cell. Physiol. 206:749-58 (2006); Forooghian & Das, "Anti-angiogenic Effects of Ribonucleic Acid Interference Targeting Vascular Endothelial Growth Factor and Hypoxia-inducible Factor-1α," Am. J. Ophthalmol. 144:761-8 (2007), each of which is hereby incorporated by reference in its entirety), and cancer (Marignol et al., "Hypoxia in Prostate Cancer: A Powerful Shield Against Tumour Destruction?" Cancer Treat. Rev. 34:313-27 (2008); Galanis et al, "Reactive Oxygen Species and HIF-1 Signalling in Cancer," Cancer Lett. 266: 12-20 (2008); Ushio-Fukai & Nakamura, "Reactive Oxygen Species and Angiogenesis: NADPH Oxidase as Target for Cancer Therapy," Cancer Lett. 266:37-52 (2008); Adamski et al, "The Cellular Adaptations to Hypoxia as Novel Therapeutic Targets in Childhood Cancer," Cancer Treat. Rev. 34:231-46 (2008); Toffoli & Michiels, "Intermittent Hypoxia Is a Key Regulator of Cancer Cell and Endothelial Cell Interplay in Tumours," FEBS J. 275:2991-3002 (2008), each of which is hereby incorporated by reference in its entirety).

Yet another embodiment of this aspect of the present invention relates to a method of reducing or preventing angiogenesis in a tissue. This method involves contacting the tissue with a peptide of the present invention under conditions effective to reduce or prevent angiogenesis in the tissue. Another embodiment of this aspect of the present invention relates to a method of inducing apoptosis of a cell. This method involves contacting the cell with a peptide of the present invention under conditions effective to induce apoptosis of the cell. Another embodiment of this aspect of the present invention relates to a method of decreasing survival and/or proliferation of a cell. This method involves contacting the cell with a peptide of the present invention under conditions effective to decrease survival and/or proliferation of the cell. Contacting (including administering) according to this aspect of the present invention can be carried out using methods that will be apparent to the skilled artisan and as described above, and can be done in vitro or in vivo.

Some example target cells, tissues and/or organs for the embodiments described above are shown in Table 2.

| Desired effect | Example Target(s) |
| --- | --- |
| Inhibit transcription of: | |
| Enolase 1 | Liver, brain, kidney, spleen, adipose, lung |
| Glucose transporter 1 | Tumor, incl. cancer |
| Glucose transporter 3 | Tumor, incl. cancer |

| Desired effect | Example Target(s) |
|---|---|
| Hexokinase 1 | Tumor, incl. cancer |
| Hexokinase 2 | Tumor, incl. cancer |
| Insulin-like growth factor 2 | Brain, liver |
| IGF binding protein 1 | Brain, liver |
| IGF binding protein 3 | Brain, liver |
| Lactate dehydrogenase A | Heart |
| Ceruloplasmin | Lymphocytes/lymphatic tissue, inflamed tissue, rheumatoid arthritic tissue |
| Erythropoietin | Liver, kidney |
| Transferrin | Liver |
| Adrenomedullin | Pheochromocytoma |
| Endothelin-1 | Endothelium |
| Nitric oxide synthase 2 | Vessels, cariovascular cells/tissue |
| Vascular endothelial growth factor | Tumor cells/tissue, incl. cancer |
| Vascular endothelial growth factor receptor FLT-1 | Tumor cells/tissue, incl. cancer |
| Vascular endothelial growth factor receptor KDR/Flk-1 | Tumor cells/tissue, incl. cancer |
| Treat or prevent: | |
| Retinal ischemia | Retina (eye) |
| Pulmonary hypertension | Lungs |
| Intrauterine growth retardation | Uterus |
| Diabetic retinopathy | Retina (eye) |
| Age-related macular degeneration | Retina (eye) |
| Diabetic macular edema | Retina (eye) |
| Angiogenesis | Tumor cells/tissue, incl. cancer |
| Decrease cell survival and/or proliferation | Cancerous cells, cells contained in the endothelial vasculature of a tissue that contains cancerous cells |

Another aspect of the present invention relates to a method of identifying an agent that potentially inhibits interaction of HIF-1α with CBP and/or p300. This method involves providing a peptide of the present invention, contacting the peptide with a test agent, and detecting whether the test agent selectively binds to the peptide, wherein a test agent that selectively binds to the peptide is identified as a potential inhibitor of interaction between HIF-1α with CBP and/or p300.

This aspect of the present invention can be carried out in a variety of ways, that will be apparent to the skilled artisan. F or example, the affinity of the test agent for the peptide of the present invention may be measured using isothermal titration calorimetry analysis, as described in Example 4 (Wiseman et al., "Rapid Measurement of Binding Constants and Heats of Binding Using a New Titration Calorimeter," Anal. Biochem. 179: 131-7 (1989); Freire et al., "Isothermal Titration Calorimetry," Anal. Chem. 62:A950-A959 (1990); Chervenak & Toone, "Calorimetric Analysis of the Binding of Lectins with Overlapping Carbohydrate-binding Ligand Specificities," Biochemistry 34:5685-95 (1995); Aki et al., "Competitive Binding of Drugs to the Multiple Binding Sites on Human Serum Albumin. A Calorimetric Study," J Thermal Anal. Calorim. 57:361-70 (1999); Graziano et al., "Linkage of Proton Binding to the Thermal Unfolding of Sso7d from the Hyperthermophilic Archaebacterium *Sulfolobus solfataricus*," Int'l J. Biol. Macromolecules 26:45-53 (1999): Pluschke & Mutz, "Use of Isothennal Titration Calorimetry in the Development of Molecularly Defined Vaccines," J. Thermal Anal. Calorim. 57:377-88 (1999); Corbell et al., "A Comparison of Biological and Calorimetric Analyses of Multivalent Glycodendrimer Ligands for Concanavalin A," Tetrahedron-Asymmetry 11:95-111 (2000), which are hereby incorporated by reference in their entirety). In one embodiment, a test agent is identified as a potential inhibitor of interaction between HIF-1α with CBP and/or p300 if the dissociation constant (Kd) for the test agent and the peptide of the invention is 50 μM or less. In another embodiment, the Kd is 200 nM or less. In yet another embodiment, the Kd is 100 nM or less.

Test agents identified as potential inhibitors of HIF-1α-p300/CREB interaction may be subjected to further testing to confirm their ability to inhibit interaction between HIF-1α with CBP and/or p300.

The present invention may be further illustrated by reference to the following examples.

EXAMPLES

Example 1

Analysis of Promoter Activity with Luciferase Assays

MDA-MB-231-HRE-Luc cells were maintained in high glucose Dulbecco's Modified Eagle's Medium ("DMEM") supplemented with 10% fetal bovine serum and 0.4 g/L Geneticin (G418 sulfate, RPI Corporation). Cells were plated in 24-well dishes (BD Falcon) at a density of $6 \times 10^4$ cells/well using 1 mL of a $6.5 \times 10^4$ cell/mL suspension. After attachment, cells were treated with 1 mL of fresh media containing HBS helices or chetomin in concentrations ranging from 10 nM to 1 μM. Cells were incubated for 6 hours at 37° C. in a humidified atmosphere with 5% $CO_2$. Hypoxia was induced by adding desferoxamine mesylate (DFO, Sigma) to a final concentration of 300 μM, and cells were incubated for an additional 18 hours. Whole cell lysates were isolated by washing the cells twice with ice cold PBS and then adding 150 μL of Cell Culture Lysis Reagent ("CCLR," Promega). Lysate was collected, centrifuged at 13,000 rpm at 4° C., aliquoted, and stored at −80° C. Luciferase assays were conducted according to the manufacturer's instructions (Promega) using a Turner TD-20e Luminometer. Relative light intensity measurements were normalized by performing a Bradford assay to determine the protein content of the lysate used in the luciferase assay. Briefly, 50 μL of cell lysate/luciferase assay reagent mix was added to 200 μL of Bradford reagent and 750 μL of Millipore water in a 1.5 mL cuvette. Protein standards were created in the range of 1 μg/mL to 10 μg/mL with the appropriate amount of a 1 mg/mL BSA solution. Absorbance was measured at 595 nm using a DU-800 spectrophotometer. The experiments were carried out in triplicate with the error bars calculated as standard error of the mean.

Example 2

Analysis of Gene Expression with qRT-PCR

Real-time qRT-PCR was used to determine the effect of HBS helices on the level of expression of VEGF and GLUT1 genes in HeLa and MCF-7 cells, both under normoxic and hypoxic conditions. For VEGF analysis, the forward primer 5'AGG CCA GCA CAT AGG AGA GA-3' (SEQ ID NO: 105) and reverse primer 5'TTT CCC TTT CCT CGA ACT GA-3' (SEQ ID NO:106) were used to amplify a 104-bp fragment from the 3'-translated region of the gene. For GLUT1 (SLC2A1) analysis, the following sequences were utilized to yield a product of 179 bp: forward sequence 5'-TAG AAA CAT GGT TTT GAA ATG C-3' (SEQ ID NO:107), reverse sequence 5'-GGT AAC AGG GAT CAA ACA GAT T-3' (SEQ ID NO:108). The levels of expression of β-glucuronidase were used as endogenous controls, since they remain unchanged under experimental conditions. The forward primer 5'-CTC ATT TGG AAT TTT GCC GAT T-3' (SEQ ID NO:109) and reverse primer 5'-CCG AGT GAA GAT CCC CTT TTT A-3' (SEQ ID NO:110) were used for this gene. Temperature cycling and detection of the SYBR green emission were performed with an ABI 7300 real-time PCR instrument. Data were analyzed with ABI Sequence Detection System, version 1.2. Statistical analysis was performed with the data from six independent experiments. The experiment was performed with Applied Biosystems SYBR Green RT-PCR master mix.

Example 3

Determination of Protein Levels with ELISA

MCF-7 cells were plated in 24 well culture dishes (BD Falcon) to a density of $1.1 \times 10^5$ cells/well using 1 mL of a $1.1 \times 10^5$ cells/mL suspension. After attachment, cells were aspirated and treated with 1 mL of media containing sporidesmins or chetomin ranging in concentration from 10 nM to 1 µM as described in Example 1. After a 6 hour incubation period at 37° C. and 5% $CO_2$ hypoxia was induced by spiking cultures with 300 nM DFO and incubating for 18 hours. Cell culture supernatants were collected, centrifuged at 10,000 rpm and 4° C., and aliquoted at 200 µL into a 96 well plate for the ELISA assay (R&D Systems), which was performed in accordance with the manufacturer's protocol. Absorbance measurements were taken at 450 nM using a Bio-Tek µQuant microplate reader. Whole cell lysate was isolated concurrently by washing the treated cells twice with ice cold PBS and then adding 150 µL per well of cell culture lysis reagent (Promega). The lysates were collected, centrifuged at 13,000 rpm at 4° C., and stored at −80° C. In parallel with the ELISA, total protein levels of whole cell lysate were determined via Bradford assay to normalize the measured VEGF concentrations in the supernatants. This process was to ascertain that VEGF inhibition is specific to blocking HIF-1α mediated transcription and not due to a global disruption of the transcriptional machinery. The samples and standards were prepared with 40 µL Bradford Reagent (Bio-Rad) and 160 µL of a protein/water mixture, and absorbance was measured at 595 nm using a Bio-Tek µQuant microplate reader.

Example 4

Figure 1C:

Design, Synthesis, and Evaluation of HBS Helices that Modulate VEGF Transcription in Cell Culture The CH1 domain of p300/CBP has a triangular geometry, as shown in FIG. 1A, and serves as a scaffold for folding of the HIF-1α C-TAD. Helix αA of HIF-1α C-TAD, shown in FIG. 1A and FIG. 1C, is critical for the interaction between the CH1 domain and HIF-1α, because mutation of its residues or hydroxylation of Asn803 is known to disrupt this complex and inhibit HIF-1α mediated transcription (Freedman et al., "Structural Basis for Recruitment of CBP/p300 by Hypoxia-inducible Factor-1α," Proc. Nat'l Acad. Sci. USA 99:5367-72 (2002); Dames et al., "Structural Basis for Hif-1α/CBP Recognition in the Cellular Hypoxic Response," Proc. Nat'l Acad. Sci. USA 99:5271-6 (2002). Development of HBS helices as potential inhibitors of VEGF transcription was begun by mimicking the aA helix region of HIF-1. This helix consists of eight residues, SYDCEVNAP (SEQ ID NO: 111), and features three residues, Asp-Cys-Glu, critical for binding with p300/CBP. Several linear peptides and their HBS α-helix analogs were designed to gauge the potential of these molecules to inhibit VEGF transcription in cell culture. Table 3 lists representative compounds designed and tested as part of these studies. Each unconstrained peptide and HBS helix was synthesized using the procedures described in (Dimartino et al., "Solid-phase Synthesis of Hydrogen-bond Surrogate-derived α-Helices," Org. Lett. 7:2389-92 (2005); Chapman & Arora, "Optimized Synthesis of Hydrogen-bond Surrogate Helices: Surprising Effects of Microwave Heating on the Activity of Grubbs Catalysts," Org. Lett. 8:5825-8 (2006)). The percent helicity of each peptide was determined using circular dichroism spectroscopy in 10 mM phosphate buffered saline as described in (Wang et al., "Evaluation of Biologically Relevant Short α-Helices Stabilized by a Mainchain Hydrogen-bond Surrogate," J. Am. Chem. Soc. 128: 9248-56 (2006)). The affinity of each peptide for p300 was measured by isothermal titration calorimetry analysis (Wiseman et al., "Rapid Measurement of Binding Constants and Heats of Binding Using a New Titration calorimeter," Anal. Biochem. 179:131-7 (1989); Freire et al., "Isothermal Titration calorimetry," Anal. Chem. 62:A950-A959 (1990); Chervenak & Toone, "Calorimetric Analysis of the Binding of Lectins with Overlapping Carhohydrate-binding Ligand Specificities," Biochemistry 34:5685-95 (1995); Aki et al., "Competitive Binding of Drugs to the Multiple Binding Sites on Human Serum Albumin. A calorimetric Study," J Thermal Anal. calorim. 57:36170 (1999); Graziano et al., "Linkage of Proton Binding to the Thermal Unfolding of Sso7d from the Hyperthermophilic Archaebacterium Sulfolobus solfataricus," Int'l J. Biol. Macromolecules 26:45-53 (1999); Pluschke & Mutz, "Use of Isothermal Titration calorimetry in the Development of Molecularly Defined Vaccines," J Thermal Anal. calorim. 57:377-88 (1999); Corbell et al., "A Comparison of Biological and calorimetric Analyses of Multivalent Glycodendrimer Ligands for Concanavalin A," Tetrahedron-Asymmetry 11:95-111 (2000)). The ability of each peptide to downregulate VEGF transcription in cell culture was evaluated by isothermal calorimetry and quantitative RT-PCR, as described above. The cytotoxicity of each peptide was determined by monitoring cellular growth and population doubling in the presence of individual peptides at 1µM concentration. Table 3 summarizes the results obtained for first generation HBS helices and peptide derivatives, and compares these values to those observed with chetomin 2.

TABLE 3

First Generation Peptides

| Compound | Sequence[a] | % Helicity[b] | $K_d$, nM[c] (ITC) | % Transcription inihibition in cell culture[d] | Cytotoxic to cells?[e] |
|---|---|---|---|---|---|
| 20 | XTAYDCEVNA-NH$_2$ (SEQ ID NO: 112) | 44% | 540 ± 40 | 0 ± 5 (Luc) | not determined |

TABLE 3-continued

First Generation Peptides

| Compound | Sequence[a] | % Helicity[b] | $K_d$, nM[c] (ITC) | % Transcription inihibition in cell culture[d] | Cytotoxic to cells?[c] |
|---|---|---|---|---|---|
| 21 |  XTAYDVEVNA-NH$_2$ (SEQ ID NO: 113) | 16% | 690 ± 60 | 0 ± 5 (Luc) | not determined |
| 22 |  XTAADCEYNAR-NH$_2$ (SEQ ID NO: 114) | 53% | 420 ± 35 | 45 ± 8 (Luc & RT-PCR) | NO |
| 23 | AcTSYDCEVNA-NH$_2$ (SEQ ID NO: 115) | 14% | 1350 ± 50 | 10 ± 5 (Luc) | not determined |
| 24 | AcTAYDCEVNA-NH$_2$ (SEQ ID NO: 116) | 15% | 1220 ± 80 | 15 ± 5 (Luc) | not determined |
| 25 | AcGTAADCEYNAR-NH$_2$ (SEQ ID NO: 117) | 15% | 825 ± 50 | 8 ± 3 (Luc & RT-PCR) | NO |
| 26 | — | — | 120 nM | 50 ± 5 | YES |

[a]X denotes a pentenoic acid residue in the HBS macrocycle.
[b]Obtained from circular dichroism studies.
[c]From isothermal titration calorimetry analysis.
[d]% Inhibition evaluated by qRT-PCR studies or luciferase assays 1 μM peptide or 200 nM chetomin, as detailed in Examples 1 and 2.

HBS peptide 20 is a direct mimic of HIF-1 αA helix but with the serine-797 residue substituted with alanine. This mutation was included to simplify the synthetic methodology, as inspection of the HIF-1/p300 structure suggested that serine-797 does not play an important role at the interface (Freedman et al., "Structural Basis for Recruitment of CBP/p300 by Hypoxia-inducible Factor-1α," Proc. Nat'l Acad. Sci. USA 99:5367-72 (2002); Dames et al., "Structural Basis for Hif-1α CBP Recognition in the Cellular Hypoxic Response," Proc. Nat'l Acad. Sci. USA 99:5271-6 (2002), which are hereby incorporated by reference in their entirety).

It was confirmed that this substitution does not perturb binding of p300, by synthesizing and characterizing linear peptides 23 and 24 (Table 3). HBS peptide 20 is significantly more helical than its corresponding unconstrained analog, peptide 24, and binds p300 with an affinity of 540 nM. HBS peptide 21 contains a valine residue in place of cysteine-800. Valine was incorporated based on the hypothesis that cysteine-800 targets a hydrophobic pocket on p300 and substitution of this residue with a more hydrophobic residue would lead to enhanced binding (Gu et al., "Molecular Mechanism of Hypoxia-inducible Factor 1α-p300 Interaction," J. Biol. Chem. 276:3550-4 (2001), which is hereby incorporated by reference in its entirety). HBS peptide 21 binds p300 with slightly lower affinity than the parent compound, HBS peptide 20, suggesting that valine may not be the optimum residue at the position typically occupied by cysteine. Although HBS helices 20 and 21 and unconstrained peptides 23 and 24 bound p300 with significant affinities, each of these peptides failed to inhibit VEGF transcription in cell culture.

It was conjectured that the inability of peptides to inhibit VEGF transcription reflected their inability to cross the cell membrane, as all of these peptides possess overall negative charges at physiological pH, and cell penetrating peptides are often rich in cationic residues (Joliot & Prochiantz, "Transduction Peptides: From Technology to Physiology," Nat. Cell Biol. 6: 189-96 (2004), which is hereby incorporated by reference in its entirety). Verdine and coworkers recently demonstrated that significant increase in cellular uptake of side-chain crosslinked helices is observed by neutralizing negative charges and including a limited set of cationic residues (Bernal et al., "Reactivation of the p53 Tumor Suppressor Pathway by a Stapled p53 Peptide," J. Am. Chem. Soc. 129:5298 (2007), which is hereby incorporated by reference in its entirety). Thus, HBS helix 22, which is derived from the parent sequence but contains a C-terminal arginine residue, was designed and studied to test whether addition of the arginine residue increases the helical content by stabilization of the helix macrodipole and potential formation of an i and i+4 ionic interaction between side chain groups of arginine and glutamic acid residues (Shi et al., "Stabilization of α-Helix Structure by Polar Side-chain Interactions: Complex Salt Bridges, Cation-π Interactions, and C—H . . . OH-bonds," Peptide Sci. 60:366-80 (2002), which is hereby incorporated by reference in its entirety). To simplify synthesis of these artificial helices, the tyrosine residue in the macrocycle was substituted with alanine (a residue that does not require side chain protection). A tyrosine residue was instead incorporated at position 802, which is occupied by valine in the wild-type sequence and not expected to be involved in binding interactions. Tyrosine or tryptophan residues were included for determination of peptide concentrations. Peptide 25 was designed as the unconstrained analog of HBS helix 22.

Figure 6A:
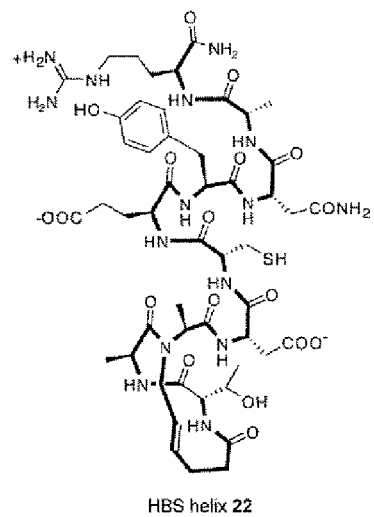
FIGS. 6A-B relate to HBS helix 22.
Figure 6B:
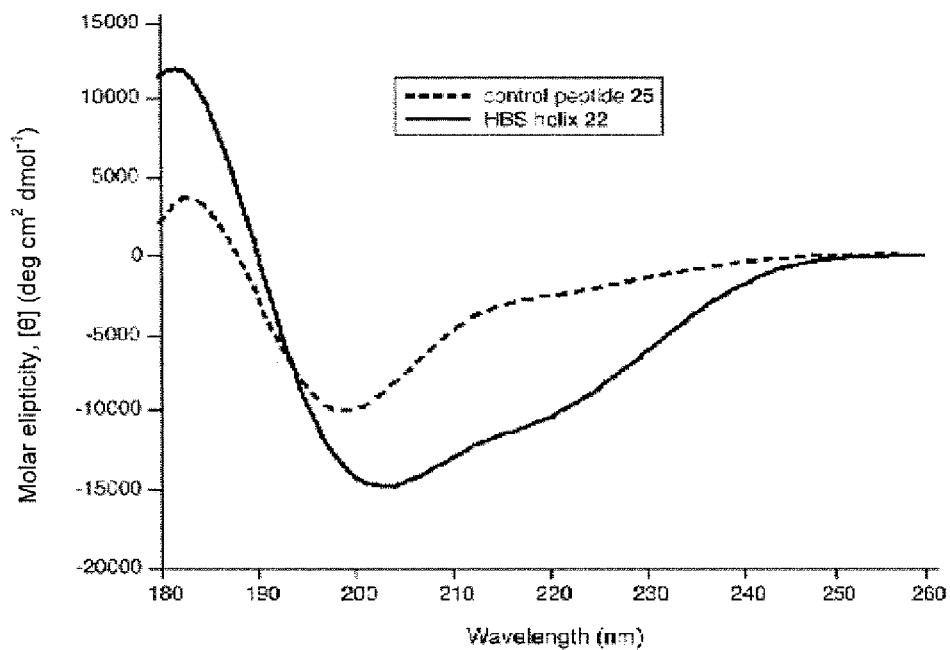

HBS helix 22 bound p300 with better affinity than HBS helices 20 and 21 and peptide 25, its corresponding unconstrained peptide, potentially because of its higher helical content as measured by circular dichroism spectroscopy (see Table 3 and FIG. 6). The CD spectra of HBS helices display a double minima at 204 and 222 nm, which is characteristic of α-helices, and the value at 222 nm indicates that the constrained peptide 22 is approximately 55% helical (Wang et al., "Evaluation of Biologically Relevant Short α-Helices Stabilized by a Main-chain Hydrogen-bond Surrogate," J. Am. Chem. Soc. 128:9248-56 (2006), which is hereby incorporated by reference in its entirety). As expected, the control peptide 25 appears to be unstructured.

Figure 7:
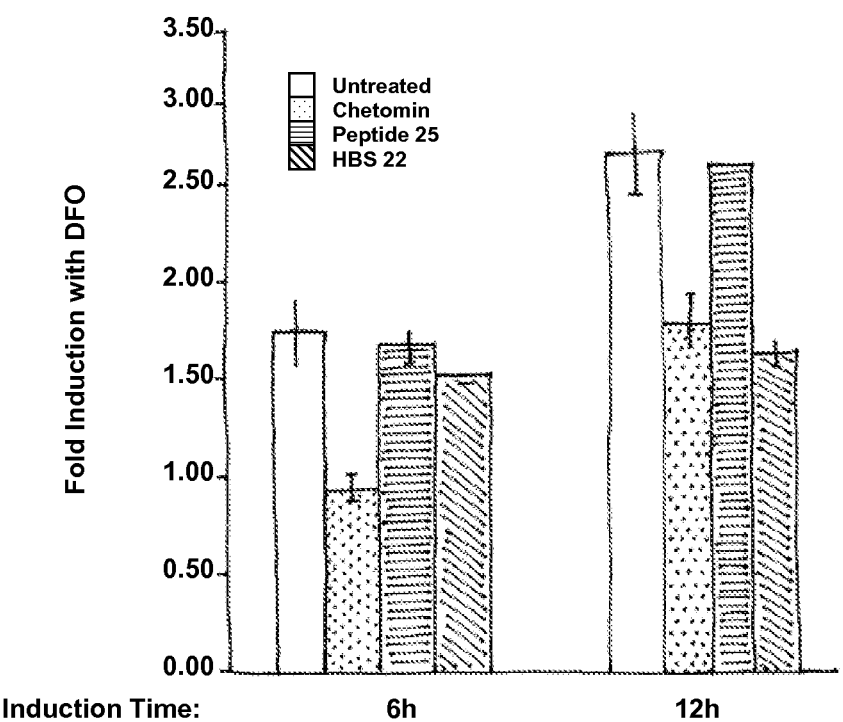
FIG. 7 is a graph of the time-dependent inhibition of the levels of VEGF gene with chetomin 2 ("chetomin"), linear control peptide 25 ("Peptide 25"), HBS peptide 22("HBS 22"), or without treatment ("untreated"), as measured by real time qRT-PCR.

As shown in Table 3 and FIG. 7, HBS helix 22 inhibited VEGF transcription in HeLa cells at levels comparable to those provided by chetomin 2, while linear control peptide 25 had a negligible effect. This result potentially reflects the proteolytic instability of the unconstrained peptide, as stabilization of peptides in α-helical conformation is expected to enhance their resistance to proteases (Tyndall et al., "Proteases Universally Recognize Beta Strands in their Active Sites," Chem. Rev. 105:973-99 (2005), which is hereby incorporated by reference in its entirety). Improvements in the proteolytic stability of HBS α-helices as compared to their unconstrained counterparts has been reported in (Wang et al., "Enhanced Metabolic Stability and Protein-binding Properties of Artificial α Helices Derived from a Hydrogen-bond Surrogate: Application to Bcl-xL," Angew. Chem. Int'l Ed. 44:65259 (2005), which is hereby incorporated by reference in its entirety). HBS helix 22 was designed to alter the overall charge of the peptide and to stabilize the helical conformation.

Figure 8:
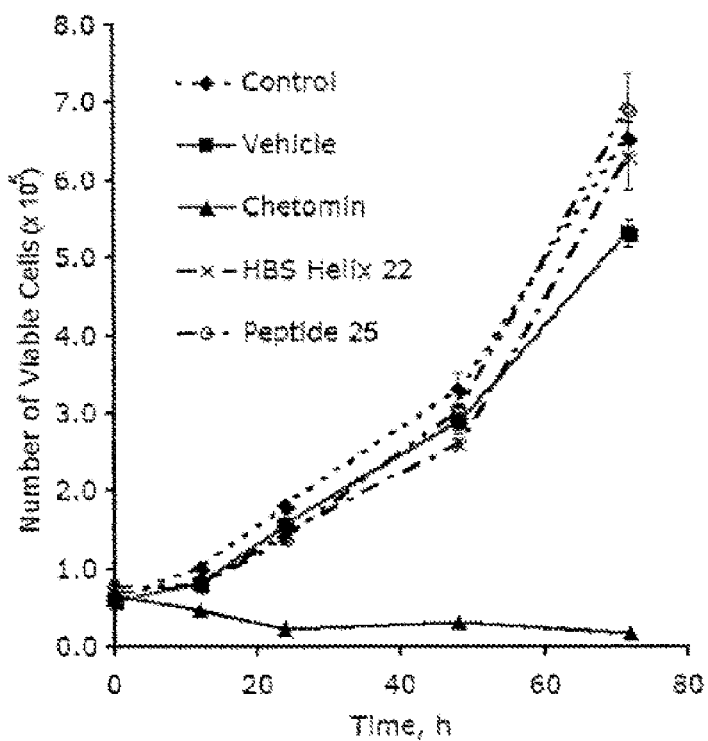
FIG. 8 is a graph of the cell density of cultures treated with: cell culture medium only ("Control"), 0.1% medium ("Vehicle"), chetomin 2, HBS helix 22, or linear control peptide 25.

Chetomin is a more potent inhibitor of VEGF transcription than HBS helix 22, as 200 nM chetomin affords roughly similar levels of inhibition as 1 µM of HBS helix 22. However, chetomin is known to be a toxic reagent while HBS helix 22 showed no apparent cytotoxicity in a cell growth assay, as shown in FIG. 8. Thus, HBS helix 22 appears to offer potent inhibition of VEGF transcription without the apparent toxicity associated with chetomin.

Example 5

Synthesis and Characterization of Second Generation HBS Helices Targeting the p300/CBP CH1 Domain The results set forth in Example 4 suggest that HBS helix 22 can efficiently inhibit HIF-1/p300 interactions in cell culture. These studies imply that the presence of the terminal arginine in HBS helix 22 may be important for increasing the effects in cell culture studies, although similar effects may be obtained by sequence substitutions on peptide 20. Additional experiments are envisioned in which analogs derived from peptides 20 and 22 are evaluated to develop optimized HBS HIF-1 mimetics, as shown in Table 4. Several compounds are preared to evaluate the role of charge on the activity of these compounds in cell culture. HBS peptide 44 is an analog of peptide 20 with a terminal arginine capable of forming an i and i+4 salt bridge with the glutamic acid residue. Analog 45 consists of two positively charged residues. Substitution of asparagine with an arginine residue in peptide 44 can afford another i and i+4 salt bridge (with the aspartic acid residue) and potentially further stabilize the helical conformation (Shi et al., "Stabilization of a Helix Structure by Polar Side-chain Interactions: Complex Salt Bridges, Cation-π Interactions, and C—H . . . OH-bonds," Peptide Sci. 60:366-80 (2002), which is hereby incorporated by reference in its entirety). HBS helix 46 is a di-arginine analog of peptide 22 and was designed to build upon the most active HBS helix. Fluorescein-labeled derivative 47 may be prepared to evaluate the cellular distribution of peptide 22. Other fluorescent analogs may be prepared as needed.

TABLE 4

Proposed HBS Peptides and Control Peptides

| Compound | Sequence | overall charge | comment |
|---|---|---|---|
| 20 |  XTAYDCEVNA-NH$_2$ (SEQ ID NO: 112) | −2 | wild-type sequence; inactive in cell culture |
| 22 |  XTAADCEYNAR-NH$_2$ (SEQ ID NO: 114) | −1 | modified sequence; active in cell culture |
| 44 |  XTAYDCEVNAR-NH$_2$ (SEQ ID NO: 118) | −1 | analog of 20 with terminal arginine |
| 45 |  XTAYDCEVRAR-NH$_2$ (SEQ ID NO: 119) | 0 | analog of 44 with N to R substitution |
| 46 |  XTAADCEYRAR-NH$_2$ (SEQ ID NO: 120) | 0 | analog of 22 with N to R substitution |

TABLE 4-continued

Proposed HBS Peptides and Control Peptides

| Compound | Sequence | overall charge | comment |
|---|---|---|---|
| 47 | XTAADCEYNARK[Flu]-NH$_2$ (SEQ ID NO: 121) | — | fluorescein-labeled 22 for cell uptake studies |
| 48 | XEELLRALD-NH$_2$ (SEQ ID NO: 122) | -2 | HIF-1 αB helix mimic |
| 49-53 | control peptides | | unconstrained peptide mimics of 44-48 |

These HBS helices have mimicked the αA helix of HIF-1. Mimics of the second helix (αB) in HIF-1 may also be evaluated. For example, HBS helix 48 represents the direct mimic of αB helix. Unconstrained peptide analogs of any HBS helix may be routinely prepared and evaluated along with the HBS helix.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A peptide of formula I:

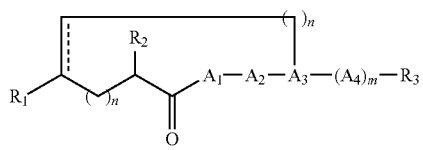 (I)

wherein
----- is a single or double carbon-carbon bond, wherein the double carbon-carbon bond is cis or trans;
each n is independently 1 or 2;
m is zero or any positive integer;
$R_1$ is an amino acid, a peptide, $-OR_4$, $-CH_2NH_2$, an alkyl group, an aryl group, or hydrogen, wherein $R_4$ is alkyl or aryl;
or $R_1$ has the formula:

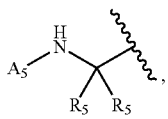

wherein $A_5$ is a peptide, an amino acid residue, an acyl group, or hydrogen; and each $R_5$ is independently an amino acid side chain, hydrogen, an alkyl group, or an aryl group;

$R_2$ is hydrogen, an amino acid side chain, an alkyl group, or an aryl group;

$R_3$ is a peptide, $-OR_6$, $-N(R_7)_2$, an alkyl group, an aryl group, or hydrogen, wherein $R_6$ is an alkyl group or an aryl group and each $R_7$ is independently an amino acid side chain, hydrogen, an alkyl group, or an aryl group; and:

(i) $A_1$ is Thr; $A_2$ is Ser or Ala; $A_3$ is Tyr or Ala; and $A_4$ comprises the formula $X^1X^2X^3X^4X^5X^6X^7$, wherein $X^1$ is Asp or Asn; $X^2$ is Val, Cys, or Ala; $X^3$ is Glu or Gln; $X^4$ is Val or Tyr; $X^5$ is Asn or Arg; $X^6$ is Ala; and $X^7$ is Arg or absent; or (ii) $A_1$ and $A_2$ are independently Glu or Gln; $A_3$ is Leu; and $A_4$ comprises the formula $LRX^8LX^9$, where L is Leu, R is Arg, $X^8$ is Ala or Tyr, and $X^9$ is Asp or Asn; and wherein the peptide modulates the interaction between HIF-1α C-TAD and the p300/CBP CH1 domain, with the proviso that the peptide sequence does not consist of the sequence Thr-Ala-Ala-Asp-Cys-Glu-Tyr-Asn-Ala-Arg-NH₂ (SEQ ID NO: 123).

2. The peptide according to claim 1, wherein the peptide is selected from the group consisting of:

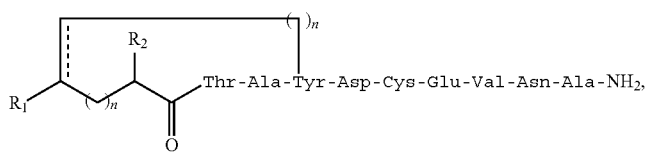

(SEQ ID NO: 1)

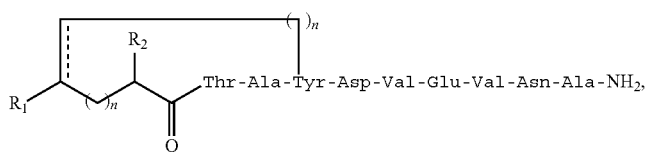

(SEQ ID NO: 2)

(SEQ ID NO: 4)

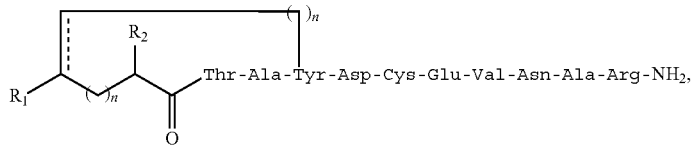
Thr-Ala-Tyr-Asp-Cys-Glu-Val-Asn-Ala-Arg-NH₂, (SEQ ID NO: 5)

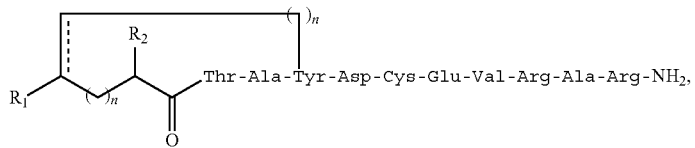
Thr-Ala-Tyr-Asp-Cys-Glu-Val-Arg-Ala-Arg-NH₂, (SEQ ID NO: 6)

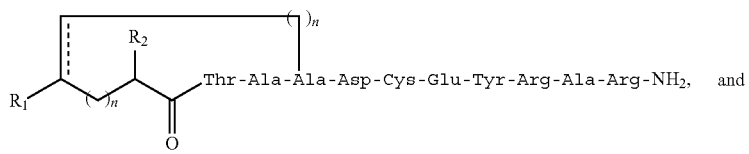
Thr-Ala-Ala-Asp-Cys-Glu-Tyr-Arg-Ala-Arg-NH₂, and (SEQ ID NO: 7)

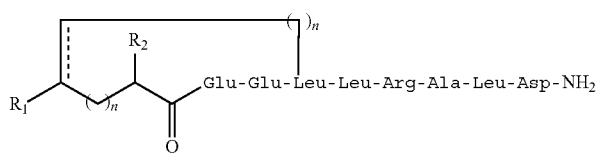
Glu-Glu-Leu-Leu-Arg-Ala-Leu-Asp-NH₂ wherein $R_2$ is hydrogen, an amino acid side chain, an alkyl group, or an aryl group.

3. A pharmaceutical composition comprising a peptide according to claim 1 and a pharmaceutically acceptable vehicle.

4. The peptide according to claim 1, wherein each n is 1.

5. The peptide according to claim 1, wherein one n is 1 and one n is 2.

6. The peptide according to claim 1, wherein each n is 2.

* * * * *